US008211644B2

(12) United States Patent
Hanna et al.

(10) Patent No.: US 8,211,644 B2
(45) Date of Patent: Jul. 3, 2012

(54) MOLECULAR BEACON-BASED METHODS FOR DETECTION OF TARGETS USING ABSCRIPTION

(75) Inventors: Michelle M. Hanna, Carlsbad, CA (US); David McCarthy, Carlsbad, CA (US)

(73) Assignee: RiboMed Biotechnologies, Inc., San Diego, CA (US)

( * ) Notice: Subject to any disclaimer, the term of this patent is extended or adjusted under 35 U.S.C. 154(b) by 317 days.

(21) Appl. No.: 12/502,217

(22) Filed: Jul. 13, 2009

(65) Prior Publication Data
US 2010/0015622 A1    Jan. 21, 2010

Related U.S. Application Data

(60) Provisional application No. 61/080,275, filed on Jul. 13, 2008.

(51) Int. Cl.
C12Q 1/70 (2006.01)
C12P 19/34 (2006.01)

(52) U.S. Cl. ............... 435/6.12; 435/91.1; 435/91.2; 435/91.51

(58) Field of Classification Search ............ 435/6.12, 435/91.2, 91.21, 91.51
See application file for complete search history.

(56) References Cited

U.S. PATENT DOCUMENTS

| | | | |
|---|---|---|---|
| 3,996,345 A | 12/1976 | Ullman et al. | |
| 4,351,760 A | 9/1982 | Khanna et al. | |
| 4,582,788 A | 4/1986 | Erlich | |
| 4,683,194 A | 7/1987 | Saiki | |
| 4,739,044 A | 4/1988 | Stabinsky | |
| 4,757,141 A | 7/1988 | Fung | |
| 4,786,600 A | 11/1988 | Kramer et al. | |
| 5,130,238 A | 7/1992 | Malek et al. | |
| 5,194,370 A | 3/1993 | Berninger et al. | |
| 5,215,899 A | 6/1993 | Dattagupta | |
| 5,246,866 A | 9/1993 | Nasu et al. | |
| 5,399,491 A | 3/1995 | Kacian et al. | |
| 5,503,979 A | 4/1996 | Kramer et al. | |
| 5,508,178 A | 4/1996 | Rose et al. | |
| 5,554,516 A | 9/1996 | Kacian et al. | |
| 5,571,669 A | 11/1996 | Lu et al. | |
| 5,595,891 A | 1/1997 | Rose et al. | |
| 5,597,694 A | 1/1997 | Munroe et al. | |
| 5,648,211 A | 7/1997 | Fraiser et al. | |
| 5,654,142 A | 8/1997 | Kievits et al. | |
| 5,679,512 A | 10/1997 | Laney et al. | |
| 5,683,879 A | 11/1997 | Laney et al. | |
| 5,744,308 A | 4/1998 | Guillou-Bonnici et al. | |
| 5,766,849 A | 6/1998 | McDonough et al. | |
| 5,824,517 A | 10/1998 | Cleuziat et al. | |
| 5,837,459 A | 11/1998 | Berg et al. | |
| 5,858,801 A | 1/1999 | Brizzolara | |
| 5,888,729 A | 3/1999 | Kacian et al. | |
| 5,888,819 A | 3/1999 | Goelct et al. | |
| 5,912,340 A | 6/1999 | Kutyavin et al. | |
| 6,008,334 A | 12/1999 | Hanna | |
| 6,103,476 A * | 8/2000 | Tyagi et al. | 435/91.2 |
| 6,107,037 A | 8/2000 | Sousa et al. | |
| 6,107,039 A | 8/2000 | Hanna et al. | |
| 6,114,519 A | 9/2000 | Cole | |
| 6,251,594 B1 | 6/2001 | Gonzalgo et al. | |
| 6,268,131 B1 | 7/2001 | Kang et al. | |
| 7,045,319 B2 * | 5/2006 | Hanna | 435/91.1 |
| 7,226,738 B2 | 6/2007 | Hanna | |
| 7,468,261 B2 | 12/2008 | Hanna | |
| 7,470,511 B2 | 12/2008 | Hanna | |
| 7,473,775 B2 | 1/2009 | Hanna | |
| 7,541,165 B2 | 6/2009 | Hanna | |
| 2002/0168641 A1 | 11/2002 | Mortensen et al. | |
| 2003/0099950 A1 | 5/2003 | Hanna | |
| 2004/0054162 A1 | 3/2004 | Hanna et al. | |
| 2005/0214796 A1 | 9/2005 | Hanna | |
| 2008/0124716 A1 | 5/2008 | Cooney et al. | |
| 2009/0298080 A1 | 12/2009 | Hanna et al. | |

FOREIGN PATENT DOCUMENTS

| | | |
|---|---|---|
| EP | 0369775 A2 | 5/1990 |
| WO | 8901050 A1 | 2/1989 |
| WO | 96041006 A1 | 12/1996 |
| WO | 03038042 A2 | 5/2003 |
| WO | 2009140666 A2 | 11/2009 |
| WO | 2009140666 A3 | 11/2009 |
| WO | 2010009060 A2 | 1/2010 |
| WO | 2010009060 A3 | 6/2010 |
| WO | 2010107716 A2 | 9/2010 |
| WO | 2010107716 A3 | 3/2011 |

OTHER PUBLICATIONS

Agrawal, et al., "Site-specific functionalization of oligodeoxynucleotides for non-radioactive labeling", Tetrahedron Lett. 31, 1990, 1543-1546.
Aiyar, "A Mismatch Bubble in Double-stranded DNA Suffices to Direct Precise Transcription Initiation by *Escherichia coli* RNA Polymerase", J. Biol. Chem. 269, 1994, 13179-131.
Chamberlin, "Bacterial DNA-Dependent RNA Polymerases", in The Enzymes, Boyer P.D., ed. Academic Press, New York, N.Y., 1982, 61, 84-86. Cheung, et al., "A Resource of Mapped Human Bacterial Artificial Chromosome Clones", Genome Research 9, 1999, 983-993.
Costas, et al., "RNA-protein crosslinking to AMP residues at internal positions in RNA with a new photocrosslinking ATP analog", Nucleic Acids Res. 23, 2000, 1849-1858.
Daube, et al., "Coupling of RNA displacement and intrinsic termination in transcription from synthetic RNA DNA bubble duplex constructs", Proc. Natl Acad. Set USA 91, 1994, 9539-9543.
Daube, et al., "Functional Transcription Elongation Complexes from Synthetic RNA-DNA Bubble Duplexes", Science 258, 1992, 1320-1324.
Dunn, et al., "Complete Nucleotide Sequence of Bacteriophage T'7 DNA and the Locations of T7 Genetic Elements", J. Mol. Biol. 166, 1982, 477-535.
Gait, "An Introduction to Modern Methods of DNA Synthesis", in Oligonucleotide synthesis: a practical approach, Gait, M.J., ed., Oxford University Press, Oxford, Great Britain, 1984, 1-22.
Gait, "Oligoribonucleotide synthesis", in Oligonucleotides and Analogues, 1992, 25-31.
Geider, et al., "An RNA transcribed from DNA at the origin of phage fd single strand to replicative form conversion", Proc. Natl. Acad. Sci. USA 75, 1978, 645-649.

(Continued)

*Primary Examiner* — Kenneth R. Horlick
*Assistant Examiner* — Joyce Tung
(74) *Attorney, Agent, or Firm* — The Law Office of Jane K. Babin, Professional Corporation; Jane K. Babin

(57) ABSTRACT

The present invention provides methods for detecting targets using an Abscription assay that exploits molecular beacon-based detection technology. The methods of the invention are highly sensitive and can be performed on a NanoDrop scale and can be multiplexed for simultaneous detection of multiple targets.

18 Claims, 20 Drawing Sheets

OTHER PUBLICATIONS

Giusti, et al., "Synthesis and Characterization of 5'-Fluorescent-dye-labeled Oligonucleotides", PCR Methods Appl. 2, 1993, 223-227.

Gohara, et al., "Poliovirus RNA-dependent RNA Polymerase (3Dpol)", J. Biol. Chem. 275, 2000, 25523-25532.

Griep, et al., "Fluorescence Energy Transfer between the Primer and the p Subunit of the DNA Polymerase in Holoenzyme", J. Biol Chem. 267, 1992, 3052-3059.

Guatelli, et al., "isothermal, in vitro amplification of nucleic acids by a multienzyme reaction modeled after retroviral replication", Proc. Natl. Acad. Sci. USA 87, 1990, 1874-1878.

Gupta, et al., "A general method for the synthesis of 3'-sulfhydryl and phosphate group containing oligonucleotides", Nucleic Acids Res 19:3019-3025, 1991, 3019-3025.

Gurevich, et al., "Preparative in Vitro mRNA Synthesis Using SP6 and T7 RNA Polymerases", Anal. Biochem. 195, 1991, 207-213.

Hanna, "Photoaffinity Cross-Linking Methods for Studying RNA-Protein Interactions", Methods Enzymol. 180, 1989, 383-409.

Hanna, "Probing the environment of nascent RNA in *Escherichia coli* transcription elongation complexes utilizing a new fluorescent ribonucleotide analog", Nucieic Acids Res 27, 1999, 1369-1376.

Hanna, et al., "Synthesis and characterization of a new photocrosslinking CTP analog and its use in photoaffinity labeling *E.coli* and T7 RNA polymerases", Nucleic Acids Res 21, 1993, 2073-2079.

Hanna, et al., "Topography of transcription: Path of the leading end of nascent RNA through the *Escherichia coli* transcription complex", Proc. Natl Acad. Sci. USA 80, 1983, 4238-4242.

He, et al., "Preparation of probe-modified RNA with 5-mercapto-UTP for analysis of protein-RNA interactions", Nucleic Acids Res. 23, 1995, 1231-1238.

Jin, "An *Escherichia coli* RNA Polymerase Defective in Transcription due to its Overproduction of Abortive Initiation Products", J. Mol. Biol- 236, 1994, 72-80.

Kinsella, et al., "RNA Polymerase: Correlation Between Transcript Length, Abortive Product Synthesis, and Formation of a Stable Ternary Complex", Biochemistry 27, 1982, 2719-2723.

Kwoh, et al., "Transcription-based amplification system and detection of amplified human immunodeficiency virus type 1 with a bead-based sandwich hybridization format", Proc. Natl. Acad. Sci. USA 86, 1989, 1173-1177.

Langer, et al., "Enzymatic synthesis of biotin-labeled polynucleotides: Novel nucleic acid affinity probes", Proc. Nad. Acad. Scl. USA 78, 1981, 6633-6637.

Lewis, et al., "Transcription of Simian Virus 40 DNA by Wheat Germ RNA Polymerase II", J. Biol. Chem. 255, 1980, 4928-4936.

Marras, et al., "Genotyping single nucleotide polymorphisms with molecular beacons", in Kwok (ed), Single nucleotide polymophisms: methods and protocols. (The Human Press Inc., Totowa, NJ) vol. 212:, 2003, 111-128.

Martin, et al., "Processivity in Early Stages of Transcription by T7 RNA Polymerase", Biochemistry 27, 1988, 3966-3974.

Meinkoth, "Hybridization of Nucleic Acids Immobilized on Solid Supports", Anal. Blochem. 138, 1984, 267-284.

Meyer, et al., "Synthesis and Characterization of a New 5-Thiol-Protected Deoxyuridine Phosphoramidite for Site-Specific Modification of DNA", Bioconjugate Chem. 7, 1996, 401-412.

Montemagno, et al., "Constructing nanomechanical devices powered by biomolecular motors", Nanotechnology 10, IOP Publishing Ltd., 1999, 225-231.

Mullis, et al., "Specific Enzymatic Amplification of DNA in Vitro: The Polymerase Chain Reaction", Cold Spring Herb. Symp. Quant. Biol. 51, 1986, 263-273.

Mullis, et al., "The Polymerase Chain Reaction: Why It Works,", in Polymerase Chain Reaction, Erlich, H.A., et al., eds., Cold Spring Harbor Laboratory Press, Cold Spring Harbor, N.Y., 1989, 237-243.

Nelson, et al., "Bifunctional oligonucleotide probes synthesized using a novel CPG support are able to detect single base pair mutations", Nucleic Acids Res. 17, 1989, 7187-7194.

Picketts, "Differential termination of primer extension: a novel, quantifiable method for detection of point mutations", Human Genetics 89, 1992, 155-157.

Pringsheim, et al., "Fluorescence of organic compounds", in Fluorescence and phosphorescence, Pringsham, P., ed., Interscience Publishers, Inc. New York, N.Y., 1949, 392-397.

Radlowski, et al., "Effect of disulfide and sulfhydryl reagents on abortive and productive elongation catalyzed by *Escherichia coli* RNA polymerase", Acta Biochim. Pol. 41, 1994, 415-419.

Saiki, et al., "Primer-Directed Enzymatic Amplification of DNA with a Thermostable DNA Polymerase", Science 239, 1988, 481-491.

Sasaki, et al., "Transcriptional sequencing: A method for DNA sequencing using RNA polymerase", Prod Natl Acad Sci USA 95, 1998, 3455-3460.

Sinha, et al., "Oligonucleotides with reporter groups attached to the 5'-terminus,", in Oligonucleotides and Analogues: A Practical Approach, Eckstein, F., ed., Oxford University Press, 1992, 185-189, 200-201.

Smithies, et al., "Detection of Targeted Gene Modifications by Polymerase Chain Reaction", in Polymerase Chain Reaction, Erlich, H.A., et al., eds., Cold Spring Harbor Laboratory Press, Cold Spring Harbor, N.Y. 1989, 199-203.

Sproat, et al., "The synthesis of protected 5'-mercapto-2', 5'-dideoxyribonucleoside-3'-0-phosphoramidites; uses of 5'-mercapto-oligodeoxyribonucleotides", Nucleic Acids Res. 15, 1987, 4837-4848.

Vet, et al., "Design and Optimization of Molecular Beacon Real Time Polymerase Chain Reaction Assays", Methods Mol. Biol. 288:, 2004, 273-90.

Walker, et al., "Isothermal in vitro amplification of DNA by a restriction enzyme/DNA polymerase system", Proc. Natl. Acad. Sci. USA 59, 1992, 392-396.

Wang, et al., "Monovalent cations differ in their effects on transcription initiation from a o-70 promoter of *Escherichia coli*", Gene 196, 1997, 95-98.

Wu, et al., "The Ligation Amplification Reaction (LAR)—Amplification of Specific DNA Sequences Using Sequential Rounds of Template-Dependent Ligation", Genomics 4, 1989, 560-569.

Zuckermann, et al., "Efficient methods for attachment of thiol specific probes to the 3'-ends of synthetic oligodeoxyribonucleotides", Nucleic Acids Res 15, 1987, 5305-5321.

* cited by examiner

```
3' Q-GGCGGCTTCCACTATATTCTCGCGATCCGCC-F 5'  (SEQ ID NO:1)
       5'GAAGGUGAUAU 3'   (SEQ ID NO:2)    11-mer abscript HaeII cleavage
3'Q-GGCGGCTTCCACTATATTCT↓CGCGATCCGCC-F 5' (SEQ ID NO:1)
      5'GAAGGUGAUAUAAGAGCGC↑TAGGCGG        (SEQ ID NO:3)

HhaI cleavage
3'Q-GGCGGCTTCCACTATATTCTC↓GCGATCCGCC-F 5' (SEQ ID NO:1)
      5'GAAGGUGAUAUAAGAGCG↑CTAGGCGG        (SEQ ID NO:3)

HinPI cleavage
3'Q-GGCGGCTTCCACTATATTCTCGC↓GATCCGCC-F 5' (SEQ ID NO:1)
      5'GAAGGUGAUAUAAGAG↑CGCTAGGCGG        (SEQ ID NO:3)
```

Figure 10A

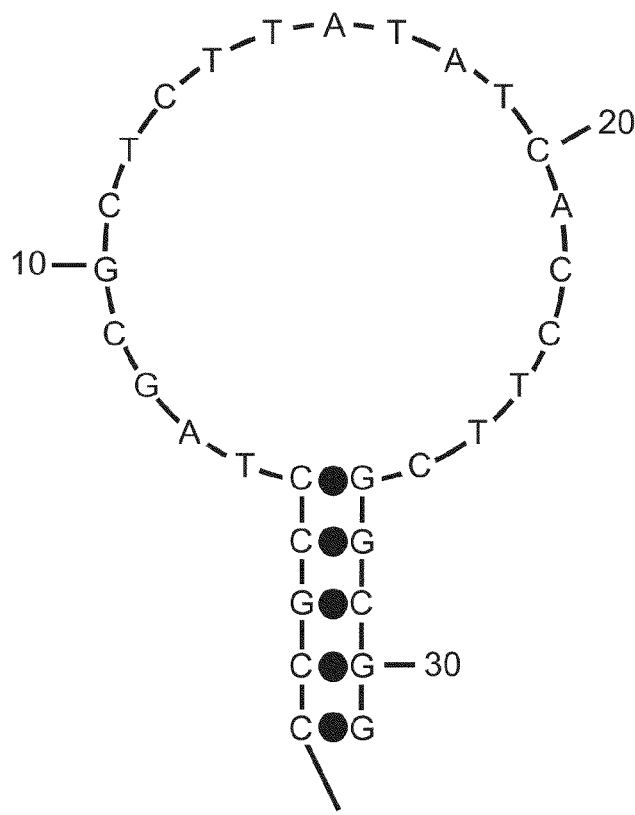

Figure 10B

5' F-CCGCCGTTTCCGAATATCACCTTCTCCGGCGG-Q   (SEQ ID NO:4)

3' BHQ1-GGCGGCCTCTTCCACTATAAGCCTTTGCCGCC 5'-FAM (SEQ ID NO:4)
            GAAGGUGAUAUTCG                       (SEQ ID NO:5)

Hpy188I cleavage
3' BHQ1-GGCGGCCTCTTCCACTATAAG↓CCTTTGCCGCC5'-FAM (SEQ ID NO:4)
            5'GAAGGUGAUAUTCG↑gaaacggcgg3'        (SEQ ID NO:6)

5' F-CCGTCGTTTCCGAATATCACCTTCTCCGACGG-Q 3' (SEQ ID NO:7)
             3'UAUCGUGGAAG 5' (SEQ ID NO:8) 11-mer Abscript 2-amino-adenine substituted   D = 2-amino-adenine
5' F-CCGTCGTTTCCGAATDTCDCCTTCTCCGACGG-Q 3' (SEQ ID NO:9)

5' F-CCGTCGTTTCCGADTDTCDCCTTCTCCGACGG-Q 3' (SEQ ID NO:10)
             3'UDUCGUGGDDG 5'(SEQ ID NO:11) 2-AA Abscript

5' CCGCTGTTTCCGAATATCACCTTCTCCAGCGG 3' (SEQ ID NO:12)

5' CCGCCATTTCCGAATATCACCTTCTCTGGCGG 3'  (SEQ ID NO:12)

3' Q-GGCGGCTTCCACTATATTCAGCCTTCCGCC-F 5'  (SEQ ID NO:14)
    5' GAAGGUGAUAU 3'                    (SEQ ID NO:2)

MOLECULAR BEACON-BASED METHODS FOR DETECTION OF TARGETS USING ABSCRIPTION

RELATED APPLICATIONS

This application claims the benefit of priority under 35 USC §119 of U.S. Provisional Applications Ser. No. 61/080,275 filed Jul. 13, 2008, the entire disclosure of which is incorporated herein by reference.

FIELD OF THE INVENTION

The present invention relates generally to the field of assays for detection of biological molecules. Specifically, the invention provides sensitive fluorescence based methods using molecular beacons for detecting a wide range of target molecules by Abscription.

SUMMARY OF THE INVENTION

The present invention provides methods for detecting and quantifying target molecules using Abscription coupled to molecular beacon opening. In one embodiment of the invention, a target (such as a protein or a nucleic acid) is detected by performing an Abscription reaction that synthesized at least one Abscript as an indication of the presence of a target. The Abscript is then hybridized to a molecular beacon that includes a probe sequence complementary to the Abscript. The hybrid that is formed, if stable, will convert the beacon to an open form. The fluorescence associated with the open beacon can be detected, thereby detecting the target. The length of the Abscript is typically in the range of 6-20 nucleotides in length, and frequently is 11 nucleotides in length.

While the longer Abscripts may be sufficient to open the beacons, the Abscript in the Abscript:beacon hybrids can also be extended with DNA polymerase and deoxyribonucleotides, to ensure that the beacons are fully opened.

Advantageously, the methods of the invention do not require purification of reaction products at each step of the method and thus can be performed in a single reaction.

These signals from these sensitive methods of the invention can be further amplified using a linear amplification procedure that includes a restriction enzyme digestion step. According to this procedure, the Abscription reaction and Abscript primer extension is performed as above, but the molecular beacon includes a sequence recognized by a restriction enzyme. Upon extension of the Abscript:beacon a double-strand DNA sequence recognized by a restriction enzyme is produced. The restriction site is then digested with the restriction enzyme to generate two fragments: a fluorophore fragment and a fragment containing the extended Abscript and the quencher. The extended Abscript fragment, which quickly dissociates from the quencher component and can hybridize to second molecule of the molecular beacon, and the extension-restriction cycle repeated to generate additional fluorphore molecules that are unlinked to the quencher.

Also provided by the invention are methods for multiplexing target detection, such a methods for detection two or more targets simultaneously. According to one such method, at least two targets are detected by:

a) performing a first Abscription reaction synthesizing a first Abscript, such that synthesizing the first Abscript indicates the presence of a first target;

b) performing a second Abscription reaction synthesizing a second Abscript having a different nucleotide sequence than the first Abscript, such that synthesizing the second Abscript indicates the presence of a second target;

c) hybridizing the first Abscript synthesized in step a) with a first molecular beacon having a first fluorophore, where the first molecular beacon includes a probe sequence complementary to the first Abscript, thereby forming a first Abscript:beacon hybrid and opening the first molecular beacon; and d) hybridizing the second Abscript synthesized in step b) with a second molecular beacon having a second fluorphore that fluoresces at a different wavelength from the first fluorophore, where the second molecular beacon includes a probe sequence complementary to the second Abscript, thereby forming a second Abscript:beacon hybrid and opening the second molecular beacon; and e) detecting fluorescence of the first and second opened molecular beacons and a indication of the presence of the two targets.

The multiplex methods can be performed in a single reaction and can include the extension and amplification steps described above, if desired.

Another multiplex method of the invention can be used to detect targets in plurality of samples, which can be arranged, for example in an array. The array can be e.g. on a solid surface such as a slide, a membrane, an arrangement of beads and the wells of a microtiter plate.

In one aspect, the method can be accomplished by:

a) performing an Abscription reaction for each of a plurality of samples, such that Abscripts are produced as an indication of the presence of the target;

b) hybridizing the Abscripts synthesized in step a) with at least one molecular beacon, where the molecular beacon includes a probe sequence complementary to the Abscript to form an Abscript:beacon hybrid to open the molecular beacon; and c) detecting fluorescence of the opened molecular beacon as an indication of the presence of the target.

This type of method of the invention is amenable to detection of the same target in multiple samples from different sources (e.g. from different tissues, subjects or at different time points). The method can also be used to detect multiple targets in the same sample by using different TSP-APC and complementary beacons for each target detected.

BRIEF DESCRIPTION OF THE DRAWINGS

FIG. 9A shows the results obtained from an Abscription reaction with an APC concentration of 4.0 ng/ml. FIG. 9B shows the results obtained from an Abscription reaction with an APC concentration of 0.4 ng/ml. FIG. 9C shows the results obtained from an Abscription reaction with an APC concentration of 0.04 ng/ml.

FIG. 10 shows the properties of a conGAA molecular beacon. FIG. 10A shows the sequence of the conGAA molecular beacon (SEQ ID NO: 1) and a complementary 11 nucleotide Abscript (SEQ ID NO:2). Restriction enzyme recognitions sites are underlined. Also shown are the product (SEQ ID NO:3) synthesized from the conGAA molecular beacon:Abscript hybrid and the cleavage sites generated by restriction enzymes HaeII, HhaI and HinPI. FIG. 10B shows the stem and loop structure of the conGAA molecular beacon ($T_m$ 50° C. in 100 mM $Na^+$, 4.3 mM $Mg^{++}$).

FIG. 11 shows the properties of a congaa-hypFQ-1 molecular beacon.

FIG. 12 shows the properties of a congaa-hypFQ-2 molecular beacon. FIG. 11A shows the sequence of the congaa-hypFQ-1 molecular beacon (SEQ ID NO:7) and a complementary 11 nucleotide Abscript (SEQ ID NO:8). Also shown are a 2-amino-adenine substituted congaa-hypFQ-2 molecular beacon (SEQ ID NO:9), a second 2-amino-adenine substituted congaa-hypFQ-2 molecular beacon (SEQ ID NO: 10) and a complementary 2-amino-adenine substituted Abscript SEQ ID NO:11).

FIG. 13 shows the properties of a congaa-hypFQ-3 molecular beacon.

FIG. 14 shows the properties of an derivative of the congaa-hypFQ-3 molecular beacon, with an A:T at the inner stem.

FIG. 15 shows the properties of a derivative HaeII beacon. FIG. 14B shows the sequence of the derivative HaeII molecular beacon (SEQ ID NO:14) and a complementary 11 nucleotide Abscript (SEQ ID NO:2).

DETAILED DESCRIPTION

Figure 1:
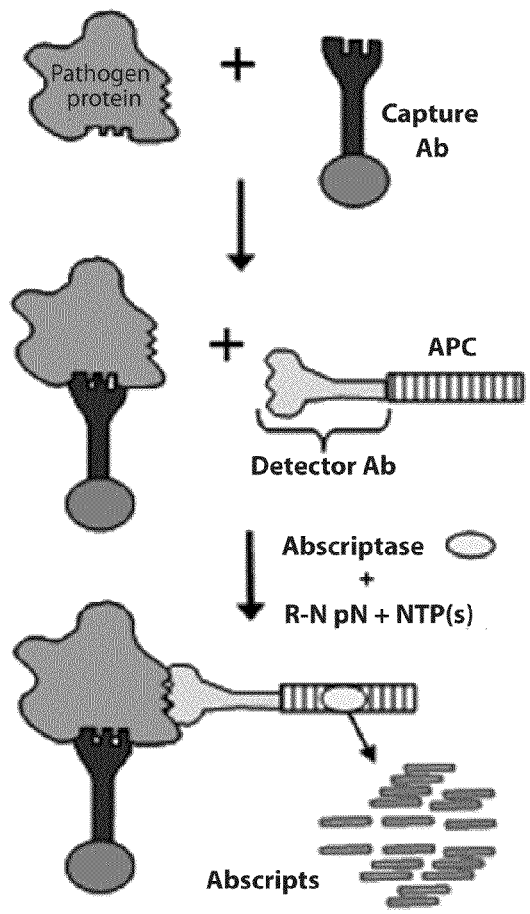
FIG. 1 illustrates an Abscription-based target detection method. Briefly, a capture antibody is attached to magnetic beads to immobilize a target, which in this case is a pathogen protein. Detector antibody is covalently attached to the DNA APC signal generator module. Ab=antibody; Abscriptase=an RNA polymerase enzyme that produces Abscript products from APCs; R-NpN=dinucleotide Abscription initiator; NTP=5' nucleoside triphosphate; Abscript=RNA oligonucleotide products of Abscription.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. As used herein, the terms "comprises," "comprising", "includes", and "including", or any other variations thereof, are intended to cover a non-exclusive inclusion, such that a process, method, composition, reaction mixture, kit, or apparatus that comprises a list of elements does not include only those elements but may include other elements not expressly listed or inherent to such process, method, composition, reaction mixture, kit, or apparatus. The section headings used herein are for organizational purposes only and are not to be construed as limiting the subject matter described.

Definitions:

Unless specific definitions are provided, the nomenclatures utilized in connection with, and the laboratory procedures and techniques of molecular biology, biochemistry, and organic chemistry described herein are those known in the art. Standard chemical and biological symbols and abbreviations are used interchangeably with the full names represented by such symbols and abbreviations. Thus, for example, the terms "deoxyribonucleic acid" and "DNA" are understood to have identical meaning. Standard techniques may be used e.g., for chemical syntheses, chemical analyses, recombinant DNA methodology, and oligonucleotide synthesis. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)); Ausubel et al., *Current Protocols in Molecular Biology* (John Wiley & Sons Inc., N.Y. (2003)), the contents of which are incorporated by reference herein in their entirety for any purpose.

"About" as used herein means that a number referred to as "about" comprises the recited number plus or minus 1-10% of that recited number. For example, "about" 50 nucleotides can mean 45-55 nucleotides or as few as 49-51 nucleotides depending on the situation. Whenever it appears herein, a numerical range, such as "45-55", refers to each integer in the given range; e.g., "45-55 nucleotides" means that the nucleic acid can contain 45 nucleotides, 46 nucleotides, etc., up to and including 55 nucleotides.

"Transcription" as used herein, refers to the enzymatic synthesis of an RNA copy of one strand of DNA (i.e., template) catalyzed by an RNA polymerase (e.g. a DNA-dependent RNA polymerase).

"Abortive transcription" is an RNA polymerase-mediated process that reiteratively synthesizes and terminates the synthesis of oligonucleotides that correspond to at least one portion of a complementary nucleic acid template sequence. Abortive oligonucleotides synthesized in vivo vary in length of nucleotides, and are complementary to a sequence at or near the transcription initiation site.

"Abscription" is a form of abortive transcription optimized for in vitro analytical use to reiteratively produce short, uniform RNA transcripts or "Abscripts" from a synthetic promoter at high frequency.

"Reiterative" refers to the repetitive synthesis of multiple identical or substantially identical copies of a sequence of interest. As used herein, "substantially identical" means that two amino acid or polynucleotide sequences differ at no more than 10% of the amino acid or nucleotide positions, typically at no more than 5%, often at more than 2%, and most frequently at no more than 1% of the of the amino acid or nucleotide positions.

"Terminator" or "transcription terminator" as used herein, refers to an RNA chain terminating compound, complex or process. A terminator of the invention can, for example, be a nucleotide analog, which can be incorporated into an RNA chain during RNA synthesis to prevent the addition of additional nucleotides to the RNA chain.

"Target" refers to any molecule of interest for which detection or quantification is desired. Targets include, without limitation, naturally occurring and synthetic nucleic acids (including modified nucleic acids), proteins (including modified proteins), carbohydrates, cells, tissues, microorganism (e.g., bacteria, viruses, etc.), receptors, ligands, analytes, and any macromolecules that can be distinguished by another molecule that binds thereto.

A "target DNA sequence" is a DNA sequence of interest for which detection, characterization or quantification is desired. The actual nucleotide sequence of the target sequence may be known or not known. Target DNAs are typically DNAs for which the CpG methylation status is interrogated. A "target DNA fragment" is a segment of DNA containing the target DNA sequence. Target DNA fragments can be produced by any method including e.g., shearing or sonication, but most typically are generated by digestion with one or more restriction endonucleases.

As used herein, a "template" is a polynucleotide from which a complementary oligo- or polynucleotide copy is synthesized.

"Synthesis" generally refers to the process of producing a nucleic acid, via chemical or enzymatic means. More typically, chemical synthesis is used for single strands of a nucleic acid. Enzyme mediated "Synthesis" encompasses both transcription and replication from a template. Synthesis includes a single copy or multiple copies of the target. "Multiple copies" means at least 2 copies. A "copy" does not necessarily mean perfect sequence complementarity or identity with the template sequence. For example, copies can include nucleotide analogs, intentional sequence alterations (such as sequence alterations introduced through a primer comprising a sequence that is hybridizable, but not complementary, to the template), and/or sequence errors that occur during synthesis.

The terms "polynucleotide" and "nucleic acid (molecule)" are used interchangeably to refer to polymeric forms of nucleotides of any length. The polynucleotides may contain deoxyribonucleotides, ribonucleotides and/or their analogs. Nucleotides may be modified or unmodified and have any three-dimensional structure, and may perform any function, known or unknown. The term "polynucleotide" includes single-, double-stranded and triple helical molecules. The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers.

"Oligonucleotide" refers to polynucleotides of between 2 and about 100 nucleotides of single- or double-stranded nucleic acid, typically DNA or RNA. Oligonucleotides are also known as oligomers or oligos and may be isolated from genes, or chemically synthesized by methods known in the art. A "primer" refers to an oligonucleotide containing at least 6 nucleotides, usually single-stranded, that provides a 3'-hydroxyl end for the initiation of enzyme-mediated nucleic acid synthesis. A "polynucleotide probe" is a polynucleotide that specifically hybridizes to a complementary polynucleotide sequence.

"Nucleic acid sequence" refers to the sequence of nucleotide bases in an oligonucleotide or polynucleotide, such as DNA or RNA. For double strand molecules, a single strand may be used to represent both strands, the complementary stand being inferred by Watson-Crick base pairing.

The terms "complementary" or "complementarity" are used in reference to a first polynucleotide (which may be an oligonucleotide) which is in "antiparallel association" with a second polynucleotide (which also may be an oligonucleotide). As used herein, the term "antiparallel association" refers to the alignment of two polynucleotides such that individual nucleotides or bases of the two associated polynucleotides are paired substantially in accordance with Watson-Crick base-pairing rules. Complementarity may be "partial," in which only some of the polynucleotides' bases are matched according to the base pairing rules. Or, there may be "complete" or "total" complementarity between the polynucleotides. Those skilled in the art of nucleic acid technology can determine duplex stability empirically by considering a number of variables, including, for example, the length of the first polynucleotide, which may be an oligonucleotide, the base composition and sequence of the first polynucleotide, and the ionic strength and incidence of mismatched base pairs.

As used herein, the term "hybridization" is used in reference to the base-pairing of complementary nucleic acids, including polynucleotides and oligonucleotides containing 6 or more nucleotides. Hybridization and the strength of hybridization (i.e., the strength of the association between the nucleic acids) is impacted by such factors as the degree of complementary between the nucleic acids, the stringency of the reaction conditions involved, the melting temperature (Tm) of the formed hybrid, and the G:C ratio within the duplex nucleic acid. Generally, "hybridization" methods involve annealing a complementary polynucleotide to a target nucleic acid (i.e., the sequence to be detected either by direct or indirect means). The ability of two polynucleotides and/or oligonucleotides containing complementary sequences to locate each other and anneal to one another through base pairing interactions is a well-recognized phenomenon.

"Microarray" and "array," are used interchangeably to refer to an arrangement of a collection of compounds, samples, or molecules such as oligo- or polynucleotides.

Arrays are typically "addressable" such that individual members of the collection have a unique, identifiable position within the arrangement. Arrays can be on a solid substrate, such as a glass slide, or on a semi-solid substrate, such as nitrocellulose membrane, or in vessels, such as tubes or microtiter plate wells. A typical arrangement for an array is an 8 row by 12 column configuration, such as with a microtiter plate.

The term "solid support" refers to any solid phase that can be used to immobilize e.g., a capture probe or other oligo- or polynucleotide, a polypeptide, an antibody or other desired molecule or complex. Suitable solid supports will be well known in the art and include, but are not limited to, the walls of wells of a reaction tray, such as a microtiter plate, the walls of test tubes, polystyrene beads, paramagnetic or non-magnetic beads, glass slides, nitrocellulose membranes, nylon membranes, and microparticles such as latex particles. Typical materials for solid supports include, but are not limited to, polyvinyl chloride (PVC), polystytrene, cellulose, nylon, latex and derivatives thereof. Further, the solid support may be coated, derivatized or otherwise modified to promote adhesion of the desired molecules and/or to deter non-specific binding or other undesired interactions. The choice of a specific "solid phase" is usually not critical and can be selected by one skilled in the art depending on the assay employed. Conveniently, the solid support can be selected to accommodate various detection methods. For example, 96 or 384 well plates can be used for assays that will be automated, for example by robotic workstations, and/or those that will be detected using, for example, a plate reader. For methods of the present invention that may involve e.g. an autoradiographic detection step utilizing a film-based visualization, the solid support may be a thin membrane, such as a nitrocellulose or nylon membrane, a gel or a thin layer chromatography plate. Suitable methods for immobilizing molecules on solid phases include ionic, hydrophobic, covalent interactions and the like, and combinations thereof However, the method of immobilization is not typically important, and may involve uncharacterized adsorbtion mechanisms. A "solid support" as used herein, may thus refer to any material which is insoluble, or can be made insoluble by a subsequent reaction. The solid support can be chosen for its intrinsic ability to attract and immobilize a capture reagent. Alternatively, the solid support can retain additional molecules which have the ability to attract and immobilize e.g., a capture reagent.

"Antibody" or "antibodies", as used herein, include naturally occurring species such as polyclonal and monoclonal antibodies as well as any antigen-binding portion, fragment or subunit of a naturally occurring molecule, such as for example Fab, Fab', and F(ab)2 fragments of an antibody. Also contemplated for use in the methods of the invention are recombinant, truncated, single chain, chimeric, and hybrid antibodies, including, but not limited to, humanized and primatized antibodies, and other non-naturally occurring antibody forms.

The present invention is based on the observations that Abscript oligonucleotide signals generated by the process of Abscription, can be used to open molecular beacons with the fluorescent emissions from the opened beacon serving as the signal for target detection and quantification in Abscription assays. According to the present invention, primary signal generation is based on an Abscription (Abortive Transcription) process in which DNA signal generators called Abortive Promoter Cassettes (APCs) are bound to targets via the target site probes (TSPs). RNA polymerase produces uniform, short RNA molecules from synthetic or natural abortive promoters in APCs as primary signals of the presence of a target. The Abscripts in turn, hybridize to and open molecular beacons, thereby generate secondary signals that are readily detectable due the fluorescent emissions of the opened beacons.

The methods of the invention offer significant advantages over current target detection methods. The methods of the invention are rapid, robust and very sensitive. Furthermore, the methods can be adapted to multiplex and automated applications.

Abscription Technology

Abscription technology is based on the observation that prior to the initiation of full-length RNA transcription, a large number of short, abortive transcripts are synthesized by RNA polymerases before full-length RNA transcripts are made. As described below, abortive transcripts are a normal by-product of the transcription process, yet are distinguishable from full-length RNA transcripts (which are the functionally informative product of the transcription process), in both size and in the manner in which they are made.

Transcription Process. Transcription is a complex and highly regulated process utilized by both eukaryotes and prokaryotes to selectively synthesize RNA transcripts from DNA templates (i.e. genes) (reviewed in Record et al. (1996) *Escherichia coli* and *Salmonella*, (Neidhart, ed.; ASM Press, Washington, DC); deHaseth et al. (1998) J. Bact. 180:3019-25; Hsu (2002) Biochim. Biophys. Acta. 1577:191-207; Murakami & Darst (2003) Curr. Opin. Struct. Biol. 13:31-39; Young et al. (2002). Cell. 109:417-420). Transcription in a cellular environment includes 5 stages: 1. Preinitiation, during which transcriptional machinery (e.g. RNA polymerase (RNAP) and transcription factors), is recruited to a promoter; 2. Initiation, during which synthesis of RNA begins; 3. Promoter Escape, during which the RNA polymerase leaves the promoter and abortive initiation stops (usually after synthesis of short RNAs approximately 2-12 nucleotides in length); 4. Elongation, during which RNAP travels processively along the template DNA strand, thereby synthesizing a full-length RNA transcript; and 5. Termination, during which RNA synthesis ceases and RNAP dissociates from the template DNA in response to sequences at the end of the transcription unit.

Production of Abortive Transcripts Prior to Full-Length RNA Transcription. Typically, RNAP fails to escape from the promoter on its first attempt and, instead, engages in multiple abortive cycles of synthesis and release of short RNA products called abortive transcripts. Only when RNAP succeeds in synthesizing an RNA product of a threshold length does RNAP irrevocably break its interactions with promoter DNA, and begin to translocate along the DNA template, processively synthesizing a full-length RNA transcript (see Hsu (2002) Biochim. Biophys. Acta. 1577:191-207; Hsu et al. (2003) Biochemistry 42: 3777-86; Vo et al. (2003) Biochemistry 42:3787-97; Vo et al. (2003) Biochemistry: 42:3798-11). Prior to promoter escape in (phase 3, above), RNAP remains bound to template DNA at or near the promoter region, thereby allowing multiple rounds of abortive synthesis in a short time.

Abscription Technology. Abscription technology exploits the natural phenomenon of abortive RNA synthesis to produce large numbers of detectable abortive transcripts (Abscripts). Abscription is an isothermal, robust, linear signal generation system based on Abortive Transcription. In an Abscription method, Abortive Promoter Cassettes (APCs) are bound to target molecules via Target Site Probes (TSPs). An RNA polymerase, such as *E. coli* RNA polymerase, then uses the APC as a template for generating large numbers of signals per target in the form of short, uniform RNA molecules or Abscripts (abortive transcripts).

Abscription detection methods have three basic steps that can be adapted to detect a wide variety of molecules of interest. First, an APC is localized to a target molecule of interest through a Target Site Probe (TSP). Second, Abscripts are synthesized from the localized APCs. Finally, Abscripts are detected as a means of target detection and may be quantified to assess the amount of a target present. The process is very efficient because the RNAP does not move away or dissociate from the promoter between rounds of abortive RNA synthesis, as it does after producing each full-length transcript. Furthermore, only uniform, short RNA signals are synthesized, which can be produced more quickly and with less effort than longer oligo- and polynucleotides.

Although the factors and conditions required for promoter escape (and hence the end of abortive synthesis), are incompletely understood, sufficient knowledge is available to create a synthetic environment that favors abortive transcript synthesis and precludes full-length RNA production. In certain embodiments, Abscription is controlled at the synthesis stage to produce Abscripts that are initiated with a defined dinucleotide initiator and then terminated after the addition of one or more NTPs. Abscript length can be limited to as short as 3 nucleotides (nt) with the use of chain terminating NTPs (e.g., 3'-O-Me-NTPs) or by omitting one or more NTPs from the reaction.

In other embodiments, Abscript length is controlled at the promoter/template stage, by providing synthetic templates that have a discrete, limited number of nucleotides available for transcription before a stop signal is reached. The uniformity of Abscript production from a single APC in a single Abscription reaction means that Abscript signals are directly proportional to the amount of target present. Thus Abscription is both a qualitative and quantitative system for measuring a target.

Target Site Probes. APCs can be coupled to wide variety of TSPs, including but not limited to oligonucleotides, polynucleotides, antibodies, ligands and other target binding species, such as mCpG binding proteins. TSPs provide specificity in Abscription methods by directing APCs to the target of interest. Abscription thus provides a robust, isothermal method for detecting and quantifying a wide range of targets.

Abortive Promoter Cassettes. "Abortive Promoter Cassettes" or "APCs" are DNA constructs containing a natural or artificial promoter recognized by an RNA polymerase to direct Abscript synthesis. In certain embodiments, the APCs of the present invention include highly abortive natural promoters or artificial promoters that contain two regions of complementary, double strand DNA that may flank a "bubble" region of unpaired, non-complementary, anti-parallel single-strand DNA. The bubble region comprises the promoter sequence on one strand and a non-complementary DNA sequence on the other strand. The non-complementarity of the bubble region facilitates Abscription by providing access to the promoter and obviating the need for RNAP to melt and unwind DNA near the synthetic promoter.

In other embodiments, the APCs of the invention contain two DNA strands that are complementary at or near their termini. Thus, the ends of such APCs of the invention have double stranded regions, which serve to join the two strands of DNA. In certain aspects, one or both strands of DNA in an APC may include a single-strand overhang for conjugation to a TSP. Thus, a typical APC includes two DNAs, however, single strand APCs that can optionally be converted to double strand molecules (e.g. by an amplification reaction), are also contemplated by the invention.

APCs can be of any length, but typically generate short fragments (<20 nucleotides). Trinucleotide Abscripts have been used extensively as these very short sequences can be rapidly synthesized and detected using mass spectrometry. However, longer Abscript lengths are also suitable for use in Abscription reactions. Longer Abscripts allow increased options for multiplexing, with different Abscripts used to simultaneously detect different targets from the same sample. APCs that produce exclusively 11-nt Abscripts have also been developed. This length is sufficient to allow detection based on hybridization of the Abscripts to molecular beacons as described herein.

The skilled artisan will recognize that disclosed APC structures are exemplary only, and other configurations are possible. The essential features of an APC of the present invention are a DNA containing an artificial or naturally abortive promoter-containing region for Abscript synthesis, a discrete template for synthesizing Abscripts of uniform size, and a means for attaching to a target site probe of the invention. APCs have been incorporated into nucleic acid TSPs that recognize complementary nucleic acids, and have been linked to antibodies that recognize e.g. protein antigens, and to methyl binding proteins that recognize methylated DNA sequences.

Non-limiting examples of APCs suitable for use as in the present invention, as described or with modifications appropriate to conjugation to a desired TSP, are provided in U.S. patent application Ser. No. 09/984,664 (filed Oct. 30, 2001) now U.S. Pat. No. 7,045,319; Ser. No. 10/425,037 (filed Apr. 29, 2003; U.S. Pat. Pub. No. 2004-0054162 A1; now abandoned); Ser. No. 10/600,581 (filed Jun. 23, 2003) now U.S. Pat. No. 7,541,165; Ser. No. 10/602,045 (filed Jun. 24, 2003) now U.S. Pat. No. 7,468,261; Ser. No. 10/607,136 (filed Jun. 27, 2003) now U.S. Pat. No. 7,226,738; Ser. No. 10/686,713 (filed Oct. 17, 2003); Ser. No. 10/976,240 (filed Oct. 29, 2004); Ser. No. 10/790,766 (filed Mar. 3, 2004) now U.S. Pat. No. 7,473,775; Ser. No. 10/488,971 (filed Oct. 18, 2004) now U.S. Pat. No. 7,470,511; and Ser. No. 10/551,775 (filed Sep. 14, 2006; U.S. Pat. Pub. No. 2006-0204964 A1; now abandoned) the contents of each of which are incorporated by reference herein in their entirety. Other APCs include natural promoters with high abortive turnover rates.

The sequences of the promoter and the initially transcribed template DNA sequence have significant effects on the lengths of the predominant abortive transcripts, as well as their rates of synthesis (Hsu (2006) Biochemistry 45:8841-54). This characteristic has been exploited to develop artificial promoters used in the APCs that are optimized to make Abscripts of different sequences and lengths at extremely high rates (>1000/min) compared to typical natural promoters. A given APC reiteratively generates a single type of short, uniform Abscript under the particular Abscription conditions selected for an assay.

Abscription can be readily adapted to high level multiplexing by varying the sequence and length of the Abscript products at the template level. Template APCs for 20 different trinucleotides with high turnover have been synthesized and at least 10 of these distinct trinucleotides can be detected in a single reaction via mass spectroscopy. Thus inherent in Abscription technology is the ability to "multiplex" or simultaneously detect multiple targets in a single reaction.

Methods for Detecting Abscripts. The signal readout for Abscription is flexible and can utilize a variety of detection technologies. As has previously been described, unlabeled trinucleotide Abscripts can be detected by HPLC, tandem HPLC-mass spectroscopy (LC-MS), Thin Layer Chromatography, capillary electrophoresis, gel electrophoresis and other methods. It is also possible to label Abscripts directly with radioactive or fluorescent labels, or affinity tags on one of the incorporated nucleotides. For example, Abscripts can be synthesized with fluorescent labels to allow direct detection by spectrofluorometry, or with affinity tags to allow the attachment of a secondary signaling system such as streptavidin-horseradish-peroxidase (HRP). APCs can be also be integrated into primers for loop-mediated isothermal amplification (LAMP) to reduce the limit of detection (LOD) for DNA and RNA to 10 molecules per sample after 15 minutes of amplification.

The present invention exploits the highly specific and sensitive molecular beacon technology for Abscript detection, enabling the use of commonly available fluorescence detection equipment for assay measurements and enhancing the sensitivity of the Abscription process. Molecular beacons do not need to be isolated from an assay mixture for detection and can thus be added directly to an Abscription assay with fluorescence signal measured in real time. As used herein "real time" refers to methods used to generate a signal and simultaneously quantify the signal, such as a signal generated for a target molecule. It enables both detection and quantification (as absolute number of copies or relative amount when normalized to target input or additional normalizing controls) of a specific target in a sample. The key feature of a real time assay is that the signal generated is quantified as it accumulates in the reaction in real time. Real time methods for detection of DNA targets are well known in the art that involve polymerase chain reaction with modified DNA oligonucleotide probes that fluoresce when hybridized with a complementary DNA. In real time PCR, amplified DNA is quantified as it accumulates in the reaction after each amplification cycle.

Frequently, real-time polymerase chain reaction is combined with reverse transcription to quantify messenger RNA (mRNA) in cells or tissues.

Advantages of Abscription Technology.

Abscription has many advantages over amplification (e.g. PCR) and other methods for detecting targets. For example, the enzymes used in PCR are easily inhibited. The usefulness of PCR for blood-based diagnostic tests is limited by the presence of several components in blood that reduce the amplification efficiency, such as hemoglobin and hemin, high concentrations of leukocyte DNA and immunoglobulin G (IgG). The usefulness of PCR for environmental and food testing is further complicated by inhibition by dust, diesel soot and components found in soil, including humic acid. Samples must therefore be carefully purified to remove such inhibitors before PCR to prevent false negative results.

Unlike systems based on target nucleic acid amplification, there are no constraints to have individual probes function together or to fit within a minimal spacing. Promoter-directed Abscription of short, reiterative, abortive transcripts does not require primers for initial RNA synthesis. Thus, initiators for Abscription are nucleotides, dinucleotide, trinucleotides, or derivatives thereof. In the Abscription-based methods of the invention, Abscripts that are produced do not become templates for further synthesis. Therefore, any errors in synthesis are not exponentially amplified and remain undetectable.

Abscription assays are resistant to environmental inhibitors and components of bodily fluids that severely inhibit PCR (see e.g., U.S. patent application Ser. No. 12/467,246, Example 1). Hemin and hemoglobin, for example, were found to have no effect on Abscription at concentrations up to 20-fold higher than the levels that inhibit PCR. Abscription reactions spiked to 30% v/v of whole blood showed no inhibition. Thus, Abscription saves time required to remove contaminants, which is necessary when using detection methods intolerant of such contaminants.

Molecular Beacon-based Abscription Technology

Abscription based target detection assays of the present invention utilize Abscripts, particularly longer Abscripts, to open molecular beacons, thereby providing a detectable fluorescent signal. The Abscripts of the present invention will generally be at least about 6 to about 25 nt, often at least about 10 to about 20 nt, and frequently at least about 11 to about 16 nt in length. The 11 nt and 14 nt Abscripts described herein are exemplary and do not in any way limit the methods of the present invention.

An exemplary Abscription assay is illustrated in FIG. 1. Briefly, the target (e.g. a protein, such as a toxin), is first captured from solution by binding to a TSP such as the capture antibody shown, that has been attached to a solid phase (e.g. a magnetic bead or microtiter plate). The solution is removed and a second antibody to which an Abortive Promoter Cassette (APC) reporter module has been attached is added (Detector Ab) and unbound detector Ab is then rinsed off. An RNA polymerase enzyme and ribonucleotide substrates needed to produce the specific short RNA encoded by the APC are added, resulting in the rapid reiterative synthesis of multiple abortive transcripts (Abscripts) from the APC without dissociation of the RNA polymerase enzyme from the APC. The Abscripts, which are produced only when target (e.g. toxin protein) is present, are detected and quantified.

Abscription technology has been used to detect a wide variety of targets including proteins, nucleic acids and modifications thereof, as described in U.S. Pat. Nos. 7,045,319 and 7,226,738; and U.S. patent application Ser. No. 10/600,581 filed Jun. 23, 2003 (now U.S. Pat. No. 7,541,165, issued Jun. 02, 2009); Ser. No. 10/602,045 filed Jun. 24, 2003 (now U.S. Pat. No. 7,468,261, issued Dec. 23, 2008); Ser. No. 10/607,136 filed on Jun. 27, 2003 (now U.S. Pat. No. 7,226,738, issued Jun. 5, 2007); Ser. No. 10/686,713 filed Oct. 17, 2003 (U.S. Pat. Pub. No. 2004-0175724 A1, published Sep. 9, 2004, now abandoned); Ser. No. 10/790,766 filed Mar. 03, 2004 (now U.S. Pat. No. 7,473,775, issued Jan. 6, 2009); Ser. No. 11/806,985 filed Jun. 05, 2007 (now abandoned); Ser. Nos. 11/531,981; 12/467,246 filed May 15, 2009 (U.S. Pat. Pub. No. 2009-0298080 A1, published Dec. 3, 2009) and Ser. No. 12/724,416, filed Sep. 16, 2010 (U.S. Pat. Pub. No. 2010-0233709 A1, published Sep. 16, 2010), which claims priority to U.S. Pat. Application No. 61/160,335 filed Mar. 15, 2009; the contents of each of which are incorporated by reference in their entirety. For nucleic acid detection, the Target Site Probe can be a nucleotide sequence complementary to the target nucleic acid that is constructed to include an APC. Proteins can be can detected using antibodies or other target-binding molecules coupled to APCs. Even such complex targets as methylated regions of genomic DNA have been detected by Abscription by using a methyl binding protein as the TSP.

The range of targets detectable by Abscription can be increased through the use of affinity-tagged reagents. For example, an affinity tag can be coupled to a TSP and used as an anchor to immobilize the target and/or as an indirect means for attaching an APC. As used herein, "affinity tag" refers to an amino acid sequence that is engineered into or joined to a polypeptide or other TSP to facilitate the purification or interactions of the affinity tagged molecule. Suitable affinity tags for use in present invention invention include His, CBP, CYD, Strep II, FLAG, HA, HPC, GST, and the like. In certain embodiments, the affinity tag is glutathione-S-transferase (GST), which permits purification of the affinity-tagged molecule on a glutathione resin by binding the GST affinity tag and subsequent elution with free glutathione. Where the affinity tag is not desired in the final TSP, a linker peptide containing a protease recognition site, such as a thrombin cleavage site, can be included between the MBD and the affinity tag. The skilled artisan will be aware of a wide variety of well known affinity tags and affinity binding partners suitable for use in Abscription reactions.

Molecular Beacons

"Molecular beacons" or "beacons" are single-stranded oligonucleotide hybridization probes that form a stem-and-loop structure. The loop contains a probe sequence that is complementary to a nucleic acid sequence, and the stem is formed by the annealing of complementary "arm" sequences that are located on either side of the probe sequence. Exemplary molecular beacons contemplated for use in the methods of the present invention sequences are described in the Examples below and in FIGS. 10-15. The skilled artisan will recognize that many additional molecular beacon sequences are commercially available and additional molecular beacon sequences can be designed for use in the methods of the present invention. A detailed discussion of the criteria for designing effective molecular beacon nucleotide sequences can be found on the world wide web at molecular-beacons.org/PA_design.html, and in Marras et al. (2003) "Genotyping single nucleotide polymorphisms with molecular beacons." (In Kwok, P. Y. (ed.), Single nucleotide polymorphisms: methods and protocols. The Humana Press Inc., Totowa, N.J., Vol. 212, pp. 111-128); and Vet et al. (2004) "Design and optimization of molecular beacon real-time polymerase chain reaction assays." (In Herdewijn, P. (ed.), Oligonucleotide synthesis: Methods and Applications. Humana Press, Totowa, N.J., Vol. 288, pp. 273-290), the contents of which are incorporated herein by reference in their entirety. Molecular beacons can also be designed using dedicated software, such as called 'Beacon Designer,' which is available from Premier Biosoft International (Palo Alto, Calif.), the contents of which is incorporated herein by reference in its entirety.

Figure 2:
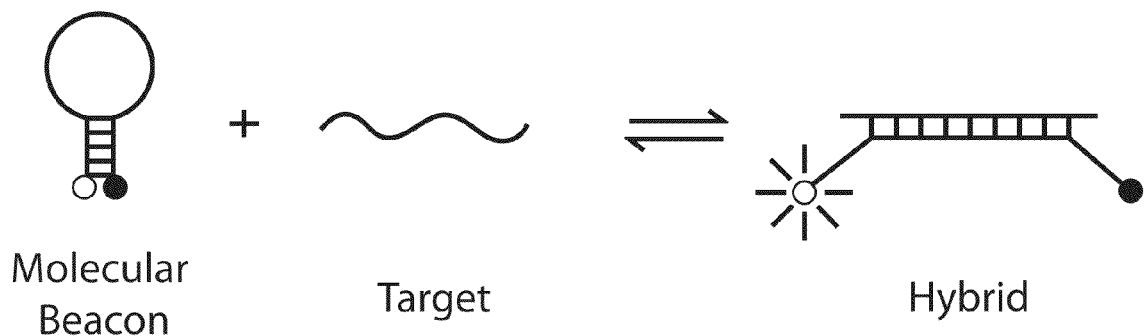
FIG. 2 illustrates a general process for detection using molecular beacons. Dark circles are used to indicate quencher molecules and open circles indicate fluorophores.

A fluorophore is covalently linked to the end of one arm of the molecular beacon sequence and a fluorescence quencher is covalently linked to the end of the other arm. Molecular beacons do not fluoresce when they are free in solution under suitable conditions of temperature and ionic strength (e.g. below the $T_m$ of the stem-loop structure). However, when molecular beacons hybridize to a nucleic acid complementary to the molecular beacon probe region, they undergo a conformational change that enables them to fluoresce brightly. In the absence of a complementary nucleic acid, the probe is dark, because the stem places the fluorophore so close to the fluorescence quencher that excitation energy of the fluorophore is transferred efficiently to the quencher, eliminating the ability of the fluorophore to emit fluoresce. When the probe encounters a suitable complementary nucleic acid molecule, it forms a probe-target hybrid that is longer and more stable than the stem hybrid. The rigidity and length of the probe-target hybrid precludes the simultaneous existence of the stem hybrid. Consequently, the molecular beacon undergoes a spontaneous conformational reorganization that forces the stem hybrid to dissociate and the fluorophore and the quencher to move away from each other, thereby allowing the fluorphore to emit fluorescence upon excitation with a suitable light source, as shown in FIG. 2.

Abscript reactions are isothermal and do not require cycles that include high temperature denaturation. Because unopened molecular beacons are dark, it is not necessary to isolate opened beacon to measure the signal in an assay. Thus, beacon-based Abscription can be performed in real-time by including molecular beacons into Abscription target detection reactions.

Detection Strategy

The present invention provides methods for detecting target-specific Abscripts based on the opening of molecular beacons by hybridization of an Abscript to the probe sequence in the molecular beacon's loop. Unlabeled Abscripts produced by Abscription (for example from a detector antibody-APC or other TSP-APC), are annealed to a molecular beacon to form an Abscript: beacon hybrid. In certain embodiments of the invention, annealing of the Abscript to the loop (probe) portion of the molecular beacon is sufficient to destabilized the stem region of the molecular beacon, thereby opening the beacon, which can then emit fluorescence energy. Longer Abscripts (typically 11 nt or longer) are needed in such embodiments to ensure stable hybridization.

In other embodiments, the Abscript acts a primer in opening the beacon. According to such embodiments, transient annealing of the 3' end of an Abscript to the loop portion of a complementary molecular beacon is sufficient to allow a DNA polymerase to stabilize the association through the addition of a few dNTPs to the Abscript primer end. Continuation of primer extension through the end of the beacon separates the fluorophore (FIG. 3 "F") from the quencher (FIG. 3 "Q") allowing excitation of the fluorophore and emission of fluorescence upon excitation by a suitable light source. Closed beacons show no fluorescence because of proximity of the quencher and the fluorophore, so background signal in the absence of a target-produced Abscript is very low. The opened fluorescent beacon can be detected without the need for sample purification or separation of the product from the substrates.

Figure 3:
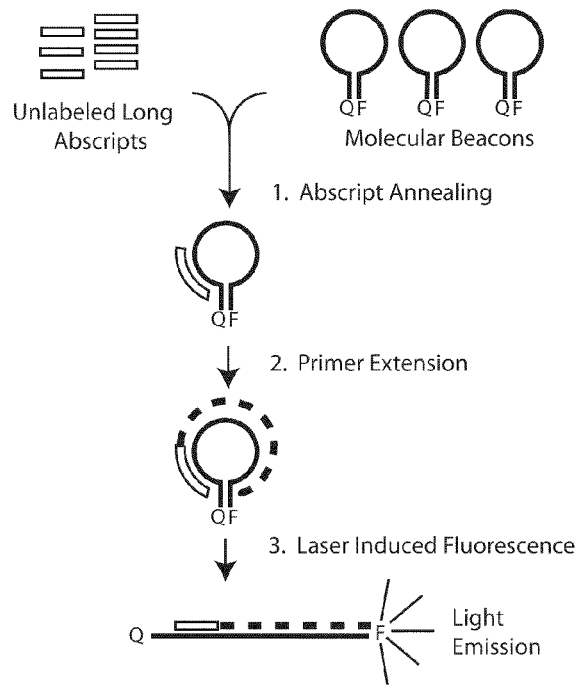
FIG. 3 illustrates an overall strategy for Abscription-based target detection using molecular beacons.

Referring to FIG. 3 which illustrates one embodiment of the invention, Abscripts are synthesized with unlabeled nucleotides as an indication of the presence of a target molecule of interest. Closed molecular beacons are present in the Abscription reaction or are added following Abscription. Closed beacons are dark due to quenching of the fluorophore (as described above). Synthesized Abscripts are annealed to the probe loop of a complementary molecular beacon, forming a hybrid. The RNA Abscript acts as a primer and can thus be extended by DNA polymerase. Annealing and extension of the Abscript by a DNA polymerase and dNTPs leads to opening of the beacon which separates the fluorophore (F) from the quencher (Q). Open beacons emit light upon irradiation (e.g. from a laser source) due to the spatial separation of the quencher and fluorophore. One fluorophore is activated per Abscript.

Like trinucleotide Abscript assays for detection by other means, the beacon approaches of the present invention allow for multiplexing when additional targets are added. Many combinations of quencher-fluorophore exist, each producing a unique color or fluorescence emission profile (see e.g. the world wide web at molecularbeacons.org and references cited therein). Fluorophores contemplated for use in the methods of the present invention include, but are not limited to: Alexa Fluor® 350; Marina Blue®; Atto 390; Alexa Fluor® 405; Pacific Blue®; Atto 425; Alexa Fluor® 430; Atto 465; DY-485XL; DY-475XL; FAM™ 494; Alexa Fluor® 488; DY-495-05; Atto 495; Oregon Green® 488; DY-480XL 500; Atto 488; Alexa Fluor® 500; Rhodamin Green®; DY-505-05; DY-500XL; DY-510XL; Oregon Green® 514; Atto 520; Alexa Fluor® 514; JOE 520; TET™ 521; CAL Fluor® Gold 540; DY-521XL; Rhodamin 6G®; Yakima Yellow® 526; Atto 532; Alexa Fluor®532; HEX 535; VIC 538; CAL Fluor Orange 560; DY-530; TAMRA™; Quasar 570; Cy3™ 550; NED™; DY-550; Atto 550; Alexa Fluor® 555; DY-555; Alexa Fluor® 546; BMN™-3; DY-547; PET®; Rhodamin Red®; Atto 565; CAL Fluor RED 590; ROX; Alexa Fluor® 568; Texas Red®; CAL Fluor Red 610; LC Red® 610; Alexa Fluor® 594; Atto 590; Atto 594; DY-600XL; DY-610; Alexa Fluor® 610; CAL Fluor Red 635; Atto 620; DY-615; LC Red 640; Atto 633; Alexa Fluor® 633; DY-630; DY-633; DY-631; LIZ 638; Atto 647N; BMN™-5; Quasar 670; DY-635; Cy5™; Alexa Fluor® 647; CEQ8000 D4; LC Red 670; DY-647 652; DY-651; Atto 655; Alexa Fluor® 660; DY-675; DY-676; Cy5.5™ 675; Alexa Fluor® 680; LC Red 705; BMN™-6; CEQ8000 D3; IRDye® 700Dx 689; DY-680; DY-681; DY-700; Alexa Fluor® 700; DY-701; DY-730; DY-731; DY-732; DY-750; Alexa Fluor® 750; CEQ8000 D2; DY-751; DY-780; DY-776; IRDye® 800CW; DY-782; and DY-781; Oyster® 556; Oyster® 645; IRDye® 700, IRDye® 800; WellRED D4; WellRED D3; WellRED D2 Dye; Rhodamine Green™; Rhodamine Red™; fluorescein; MAX 550 531 560 JOE NHS Ester (like Vic); TYE™ 563; TEX 615; TYE™ 665; TYE 705; ODIPY 493/503™; BODIPY 558/568™; BODIPY 564/570™; BODIPY 576/589™; BODIPY 581/591™; BODIPY TR-X™; BODIPY-530/ 550™; Carboxy-X-Rhodamine™; Carboxynaphthofluorescein; Carboxyrhodamine 6G™; Cascade Blue™; 7-Methoxycoumarin; 6-JOE; 7-Aminocoumarin-X; and 2',4',5',7'-Tetrabromosulfonefluorescein.

A variety of quenchers are also available, including: Dabcyl; TAMRA; Black Hole Quenchers™; BHQ-1®; BHQ-2®; BBQ-650; DDQ-1; Iowa Black RQ™; Iowa Black FQ™; QSY-21®; QSY-35®; QSY-7®; QSY-9®; QXL™ 490; QXL™ 570; QXL™ 610; QXL™ 670; QXL™ 680; DNP; and EDANS. The skilled artisan will recognize that individual fluorophores and quenchers are each optimally active at a particular wavelength or range of wavelengths. Therefore, fluorphore and quencher pairs must be chosen such that the fluorophore's optimal excitation and emission spectra are matched to the quencher's effective range.

Figure 4:
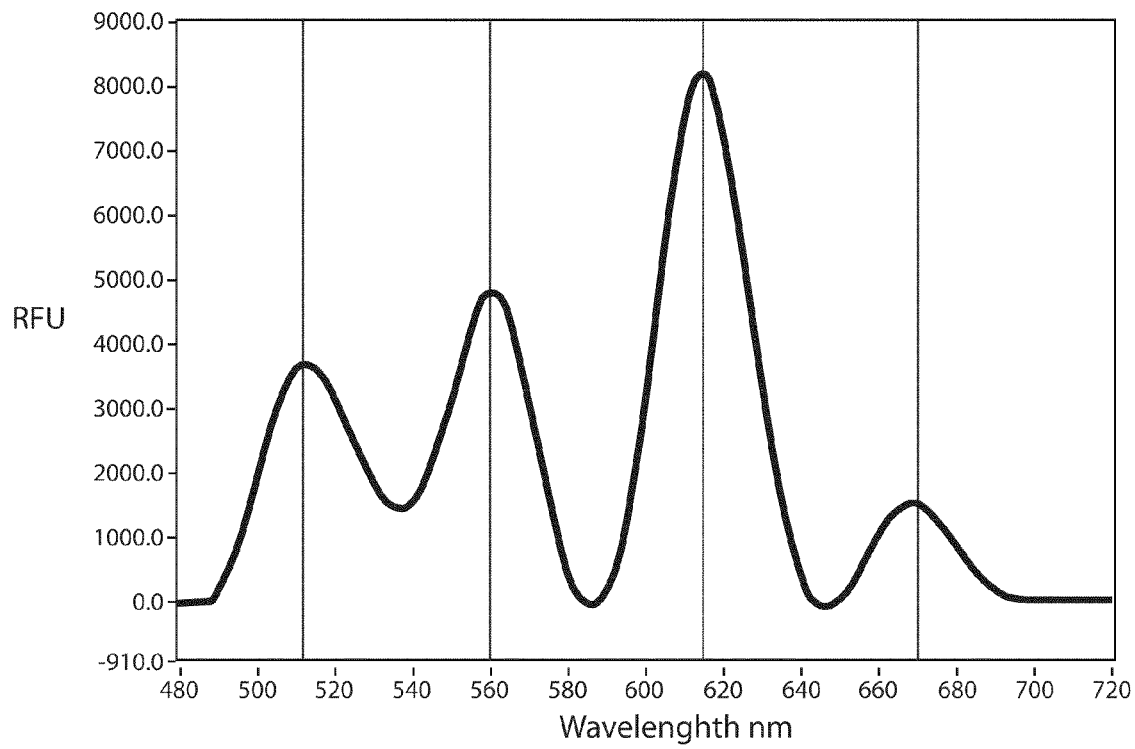
FIG. 4 is a graph showing the relative fluorescent intensity (RFU) of four different molecular beacons.

According to the methods of the present invention, several beacons can be opened in a single solution without the need for fractionation. The fluorophores listed above represent a virtual rainbow of emission colors (emission wavelengths). Fluorescence from a blue fluorophores can be easily discriminated, for example from that of a red fluorphore. FIG. 4 shows the potential for detecting four different targets from a sample with a single reading by the opening of 4 different molecular beacons each containing a fluorophore of a different color (emission wavelengths). The readout shown in FIG. 4 was obtained using only a 2 microliter sample in a NanoDrop fluorospectrometer (Thermo Scientific) in just 10 seconds. The skilled artisan will be aware of additional instrumentation for detecting fluorescence including various fluorospectrometers, fluorescence microscopes, fluorescence array readers and real time thermocycling assay detectors.

Figure 5:
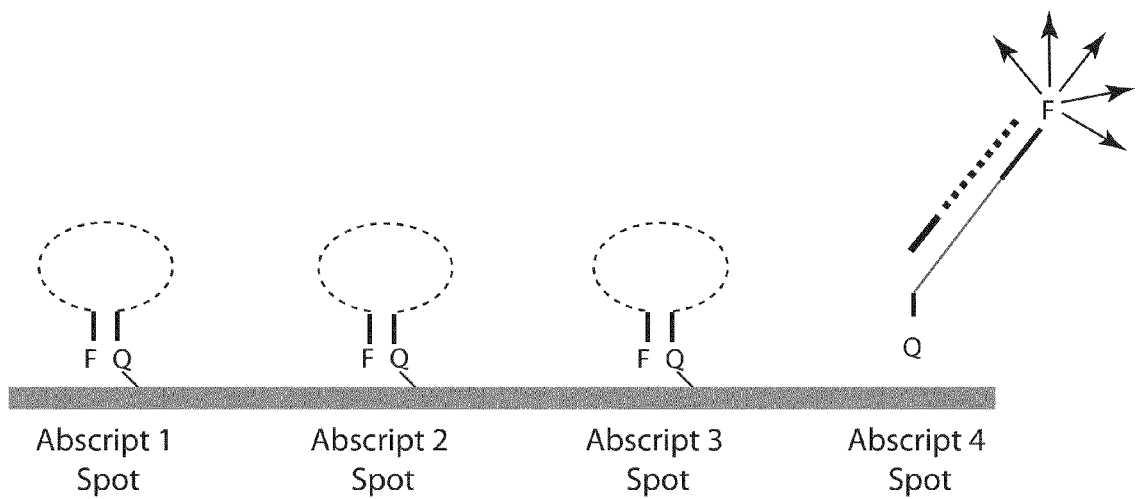
FIG. 5 illustrates a multiplex target detection method using molecular beacons.

Multiplexing can also be accomplished using methods of the present invention with a single fluorphore attached to several different beacons. As illustrated in FIG. 5, individual beacons having the same fluorophore but different probe (loop) sequences can be, for example, spotted or otherwise immobilized onto a solid phase (e.g. chips, plates, slides and the like), or in microtiter plates, such as in an array pattern. Individual Abscript-containing samples can then be added to the beacon array and the resulting fluorescence detected. An exemplary embodiment of this type of Abscription-beacon multiplexing is illustrated in FIG. 5.

In addition to direct detection by fluorescence intensity, the molecular beacon approach is amenable to capillary electrophoresis (CE) based detection without sample fractionation or sample clean-up. Moreover, the molecular beacon approach (with or without NanoDrop detection) has several advantages over the direct incorporation of fluorophore-labeled nucleotides into Abscripts (e.g. production of CY5-labeled trinucleotide Abscripts) followed by CE detection. First, in the beacon approach there is no reduction in the rate of Abscript synthesis as would occur with the direct incorporation of a CY5-initiator. A typical 11 nt Abscript is synthesized with unlabeled substrates and accumulates at a faster rate than shorter CY5-labled trinucleotide Abscripts. Second, it is not necessary to use high concentrations of dye molecules when detection is based on molecular beacons. Molecular beacons can used be at concentrations below 100 nM while CY5-dinucleotide substrates must be present at a minimal concentration of 100 µM to support the production of labeled trinucleotide. Third, the NanoDrop instrument allows direct fluorescence intensity measurements of reaction mixtures without the need for fractionation, as is required for CE detection. Fourth, NanoDrop readings are very rapid (10 seconds) compared to the CE (5 minutes or more). Finally, the NanoDrop detector is much simpler to use than CE, with few moving parts, thereby requiring less maintenance or training of the end user.

Increased Sensitivity Through a Molecular Beacon Cascade System

Figure 6:
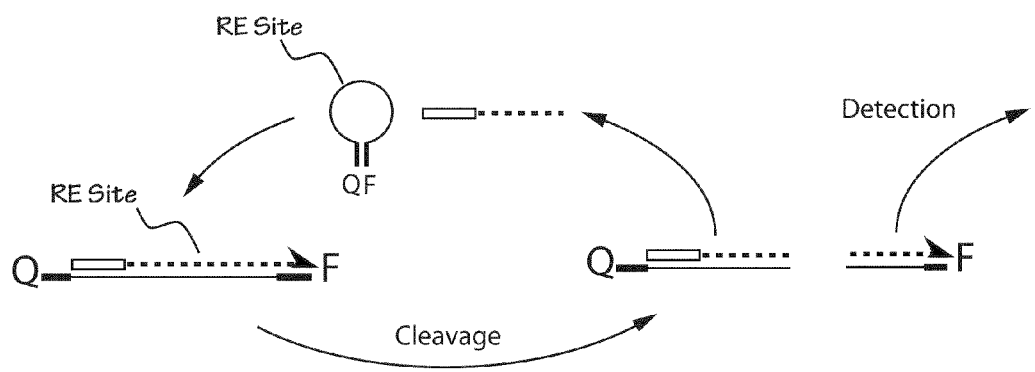
FIG. 6 is a diagram showing a strategy for amplifying a molecular beacon signal from Abscripts.

The sensitivities of Abscript-beacon methods of the invention are very high, as described below in Example 2, and detection as few as about 1,600 target molecules can be achieved. However, where the limits of detection are insufficient or a target-containing sample is in limited supply, the present invention provides methods for increased sensitivity through a signal amplification procedure, as illustrated in FIG. 6. According to this procedure, beacons are designed to incorporate a restriction enzyme recognition site within the probe loop region. In certain embodiments, the restriction site is adjacent to, but outside of and 5' of the beacon probe sequence that is complementary to the Abscript. When an Abscript anneals to the molecular beacon, thereby forming a double-strand nucleic acid region, the restriction site is not formed. Extension of the Abscript primer is required to generate a fully double-stranded restriction site that is susceptible to cleavage by the restriction endonuclease.

Following extension, cleavage releases the fluorophore from the quencher and truncates the extended Abscript primer. The fluorphore is then detected as it is being released or at the end of the reaction. The staggered cuts leave a relatively short quencher-beacon strand annealed to an Abscript strand that is typically 1-10, and often about 5 nt longer than the unextended Abscript. According to this procedure, the melting temperature of the cleaved Abscript: quencher duplex is lower than the reaction temperature leading to the rapid dissociation of these strands. The free Abscript-primer can thus be recycled for another round of hybridization to an intact beacon. The association of the Abscript-primer is stabilized due to the formation of about 5 extra base pairs involving the dNMPs that were added to the Abscript. Subsequent extension of the primer and cleavage by the restriction endonuclease leads to another round of beacon opening. The net effect is that each Abscript activates multiple fluorophores, resulting in linear signal amplification. Exemplary restriction endonuclease site-containing molecular beacons are described in Example 5.

EXAMPLES

Example 1

Detection of Abscripts Using Molecular Beacons

An Abscription reaction yielding a 11 nucleotide Abscript was performed as previously described (see e.g. U.S. Pat. No.

Figure 7:
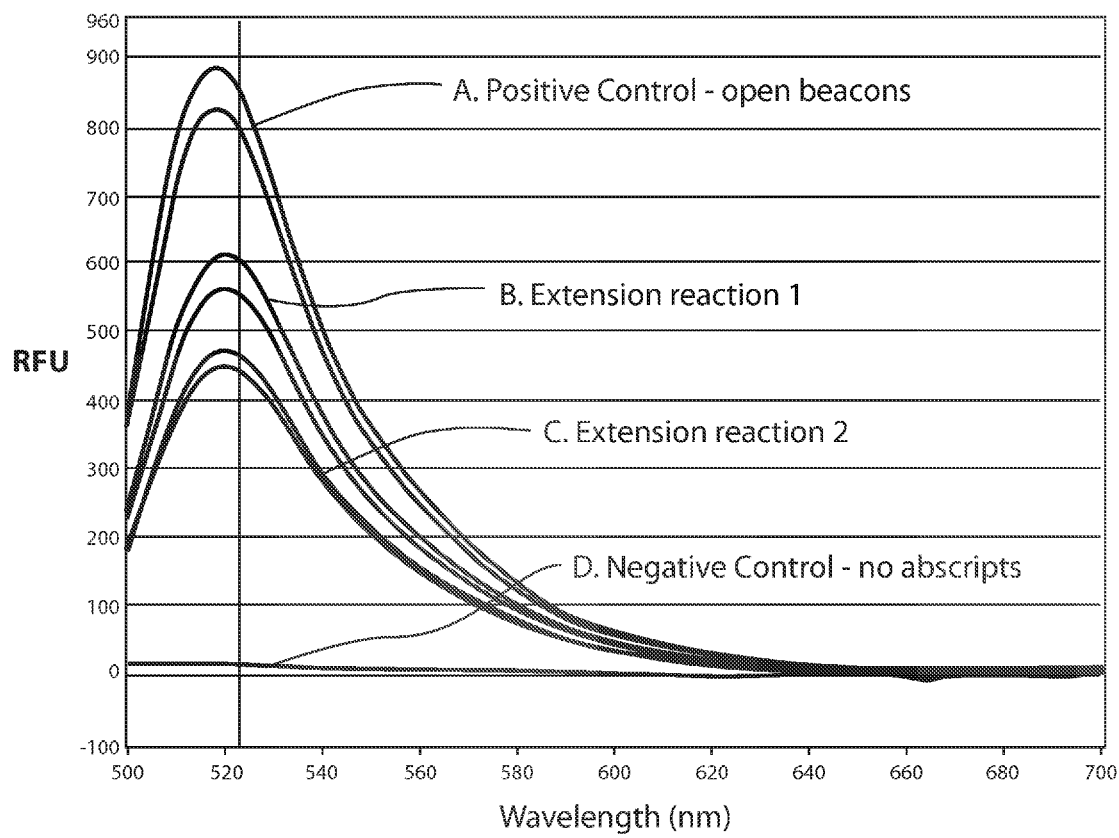
FIG. 7 shows the results of detecting Abscripts with molecular beacons.

7,045,319) for 5 min followed by a 1:1 dilution into a buffer containing a DNA polymerase, a molecular beacon and dNTPs. The 11 nt long Abscript was annealed to a complementary segment of a molecular beacon. Elongation of the Abscript through the end of the beacon was accomplished using a DNA polymerase according to manufacturer's directions to produce a 26 nt extended Abscript. FIG. 7 shows the detection of fluorescence from the beacons that were opened by Abscript-extension. A complementary nonlabeled DNA that quantitatively opened all available beacons was included in parallel as a positive control (A—Positive Control). Two different DNA polymerases with different activities were used to perform Abscript extension (B—Extension Reaction 1 and C—Extension Reaction 2). Reaction 2 contained a DNA polymerase that was exposed to elevated temperature. A partial loss of activity could be detected versus the fully active DNA polymerase in reaction 1. The negative control (D—Negative Control) omitted the promoter for Abscript synthesis and showed very little background fluorescence in the presence of the Abscription and primer extension reagents.

As shown in FIG. 7, the positive control demonstrated saturating beacon opening mediated by an annealed synthetic DNA complementary to the beacon. Extension reactions 1 and 2 contained DNA polymerases of differing activity. The negative control was based on an Abscription reaction without an abortive promoter. All reactions were performed in duplicate. Fluorescence intensities were measured with a NanoDrop fluorescence reader (Thermo Scientific, Wilmington, Del.).

Example 2

Titration of Molecular Beacon Opening by Abscripts

Figure 9A:
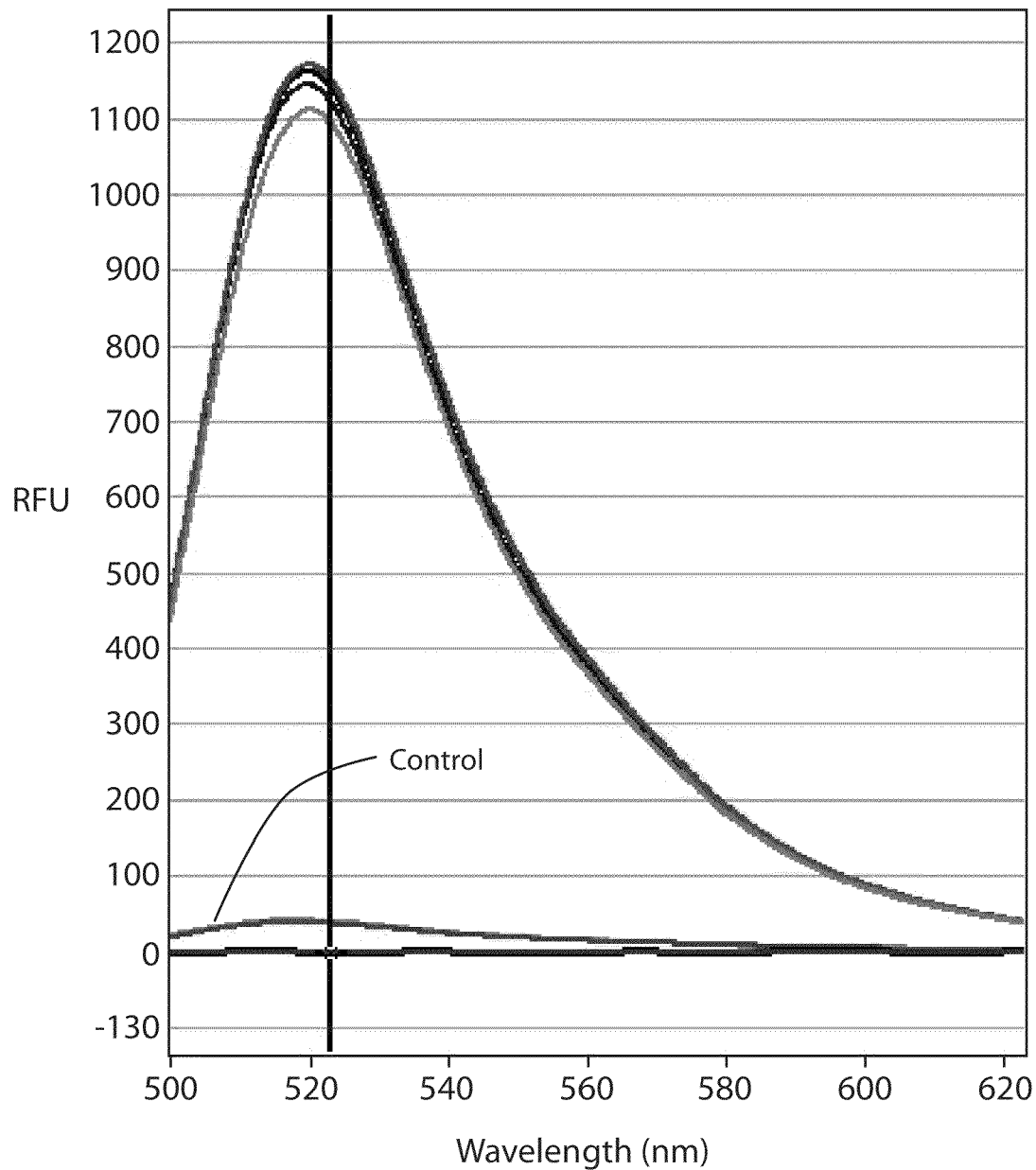
FIGS. 9A-9C are graphs comparing the detection of various amounts of Abscripts using molecular beacons.
Figure 9B:
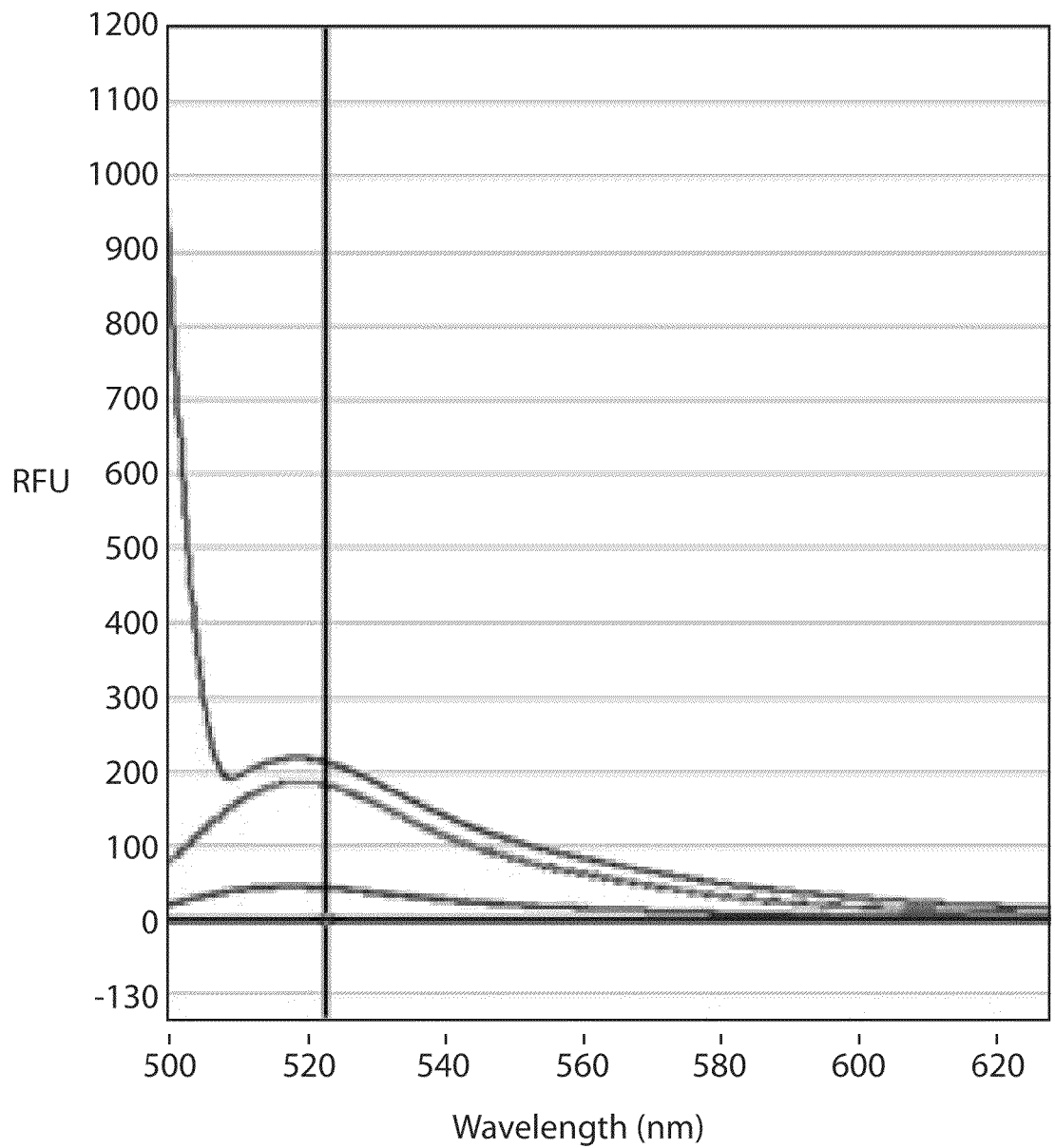
Figure 9C:
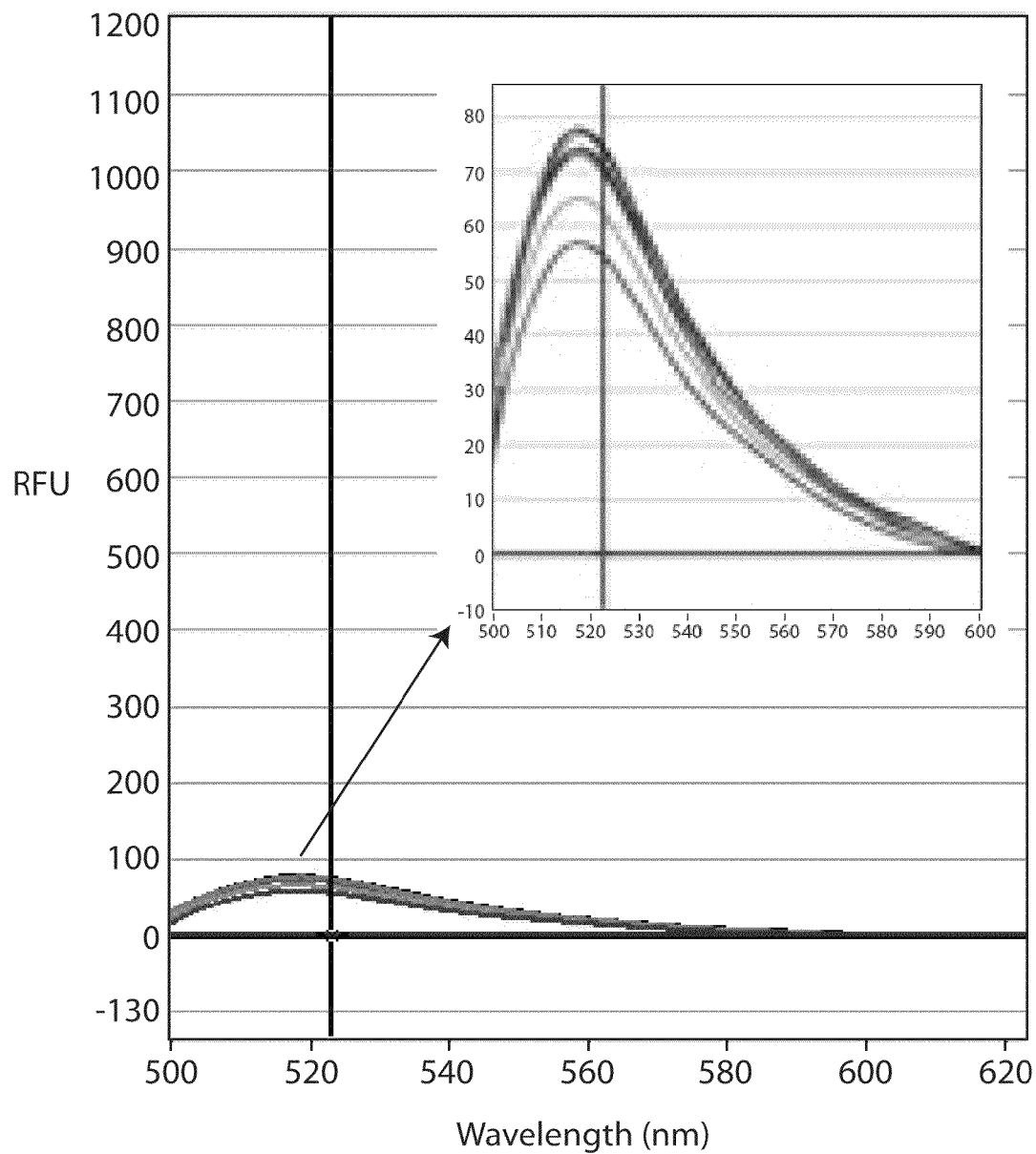
Figure 10C:
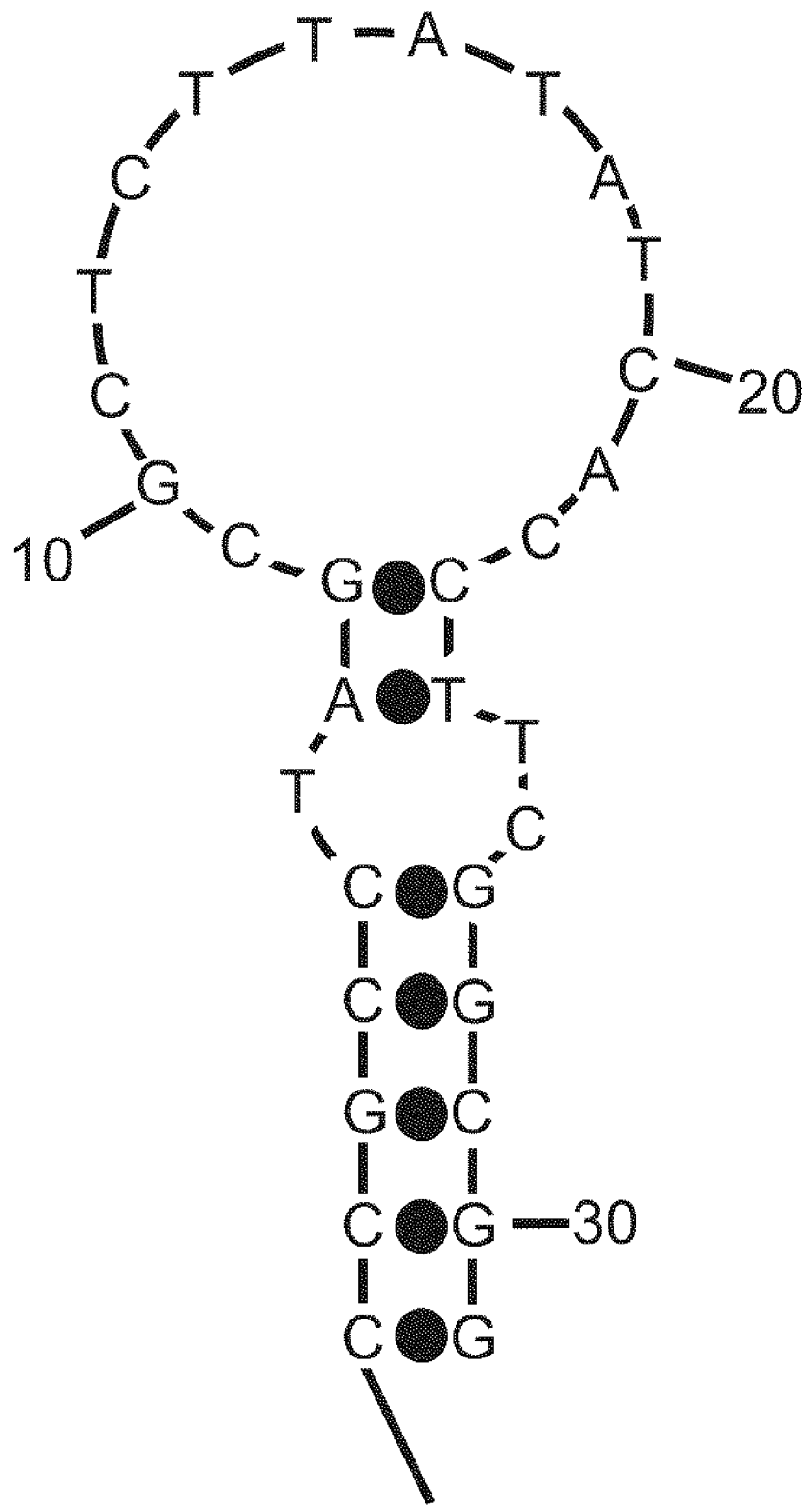
FIG. 10C shows an alternate stem and loop structure of the conGAA molecular beacon ($T_m$ 62.3° C. in 50 mM $K^+$, 5 mM $Mg^{++}$).

The sensitivity of the molecular beacon approach was tested by titrating a synthetic DNA that mimicked the interaction of the extended Abscript with a molecular beacon, followed by measuring the fluorescence intensity with the NanoDrop reader, as shown in FIG. 9. A reaction containing a closed molecular beacon at a concentration of 200 nM was incubated with the synthetic DNA at 35° C. followed by 5 min at 50° C. under Abscription-Extension conditions as in Example 1. Fluorescence signal intensity correlated with the opening of beacons by the annealed DNA. At a concentration of 200 nM, closed beacons showed very low background fluorescence due to the close association of fluorophore and quencher. Synthetic DNA could be detected at concentrations as low as 1 nM.

Example 3

Sensitivity of Molecular Beacon Opening by Abscription

Figure 8:
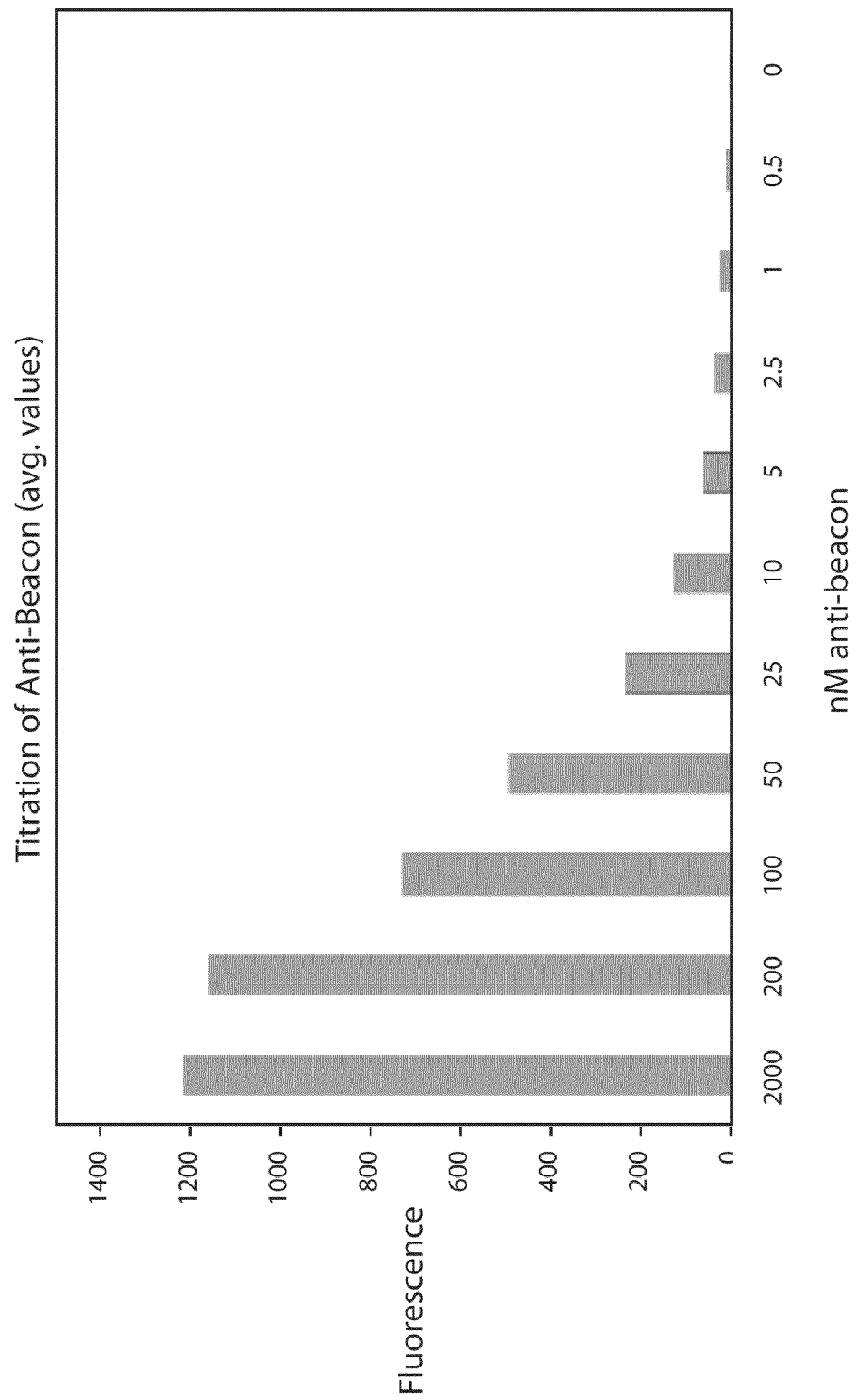
FIG. 8 shows fluorescence based detection of an unlabeled DNA complementary to a molecular beacon.

Abscription was performed as in Example 1 at APC concentrations equivalent to 4.0, 0.4 and 0.04 ng/ml of a 150 kDa template, producing an 11 nt Abscript. The opening of a fluorescein labeled molecular beacon by the 11 nt Abscript was carried out after only 5 minutes of Abscription. Fluorescence measurements were taken using a NanoDrop Fluorospectrometer and were not adjusted for background fluorescence. Four separate reactions were performed for each concentration and the fluorescence was measured sequentially. Spectra were then overlaid on the graph shown in FIG. 8. Note that for the 0.4 ng/ml reactions, three of the readings were so similar that they appear to be a single line. The 4.0 and 0.4 ng/ml templates were readily and reproducibly detected. The 0.04 ng/ml signal is above background and although low, was reproducible.

Example 4

Target Detection by Abscript Opening of Molecular Beacon

A sample containing a target is incubated with a Target Site Probe linked to an APC to allow targets to bind the TSP. The TSP is immobilized on magnetic beads, such that the bound target can be captured and unbound substances in the sample are washed away. Abscription is performed by adding RNA polymerase, polymerase buffer and NTPs. An excess amount of molecular beacons, DNA polymerase and dNTPs are then added to the Abscription reaction and the incubation continued at 35° C. followed by incubation for 5 min at 50° C. Fluorescence is detected in the sample as an indicator of the presence of the target in the sample.

Example 5

Fluorescent Signal Amplification with Restriction Endonuclease-containing Molecular Beacons An Abscription reaction is performed as described above, generating an 11-mer Abscript having the sequence 5' GAAGGUGAUAU 3' (SEQ ID NO:2). This Abscript, in conjunction with the conGAA molecular beacon (FIG. 10), will give restriction fragments having the properties listed below in Table 1 when cleaved with HaeII, HhaI, and HinP1I.

TABLE 1

Properties of conGAA Abscript-Beacon Restriction Digestion Products

| Abscript | $T_m$ at 50 mM Na | $T_m$ at 75 mM Na | $T_m$ at 100 mM Na (plus MgCl$_2$ 4.3 mM) |
| --- | --- | --- | --- |
| GAAGGUGAUAU | 26.2 | 29 | 30.8 (31.89) |
| absc + A | 29.5 | 32.4 | 34.2 |
| absc + AA | 31.9 | 34.9 | 36.9 |
| absc + AAG | 35.2 | 38.2 | 38.8 |
| $T_m$ of HaeII cleaved Abscript strand to the cleaved beacon strand | | | |
| absc + AAGA | 37.8 | 40.9 | 41.9 (44.23) HaeII |
| absc + AAGAG | 40.2 | 43.3 | 44.7, (47.2) HhaI, HinP1I |
| absc + AAGAGC | 44.5 | 47.6 | 48.2 |
| $T_m$ of HaeII cleaved Abscript strand to an uncleaved beacon | | | |
| absc + AAGAGCG | 48 | 51.1 | 52.1 (55.9) HhaI |
| absc + AAGAGCGC | 51.3 | 54.4 | 55.2 (59.5) HaeII |
| absc + AAGAGCGCT | 52.7 | 55.9 | 58 |
| absc + AAGAGCGCTA | 52.4 | 55.6 | 57.7 |

The Abscription reaction is diluted 1:1 to give a final buffer concentration of 50 mM NaCl, 4.3 mM MgCl$_2$. To the Abscription reaction is added an excess of the conGAA molecular beacon (FIG. 10), DNA polymerase and HaeII restriction enzyme, and the reaction is incubated at 37° C. for min to anneal and elongate the Abscript primer, and cleave the resulting double-stranded beacon at the corresponding HaeII restriction site. The 37° C. incubation is followed by incubation at 50° C. to ensure that the cleaved, elongated Abscript dissociates from the quencher-containing beacon strand. The temperature cycling is repeated for about 20 cycles, during which the fluorescence from the fluorophore-containing beacon strand is continually monitored. The fluorescence signal from the temperature cycles reactions is at least 10 fold higher than a control reaction that to which restriction enzyme is not added.

Example 6

Multiplex Detection of Targets by Abscription and Fluorescent Molecular Beacons

Abscription reactions are performed on samples from a variety of sources as described above. The reactions are performed in the wells of microtiter dishes, with each well containing a different sample and the same TSP-APC for detection of the same target. Samples containing the target generate an 11-mer Abscript having the sequence 5' GAAG-GUGAUAU 3' (SEQ ID NO:2). The reactions in each well are diluted 1:1 to give a final buffer concentration of 50 mM NaCl, 4.3 mM $MgCl_2$. To the each well is added an excess of the conGAA molecular beacon (FIG. 10), DNA polymerase and HaeII restriction enzyme, and the reaction is incubated at 37° C. for min to anneal and elongate the Abscript primer, and, cleave the resulting double-stranded beacon at the corresponding HaeII restriction site. The 37° C. incubation is followed by incubation at 50° C. to ensure that the cleaved, elongated Abscript dissociates from the quencher-containing beacon strand. The temperature cycling is repeated for about 20 cycles, during which the fluorescence from the fluorophore-containing beacon strand is continually monitored in a multi-well plate thermocycler with real-time fluorescence detection, such as the Applied Biosystems 7900HT Fast Real-Time PCR System.

Example 7

Exemplary Molecular Beacons Suitable for Use Abscription Methods

The following are exemplary molecular beacons that have been designed for use with the Abscription methods described herein.

Figures 11A, 11B:
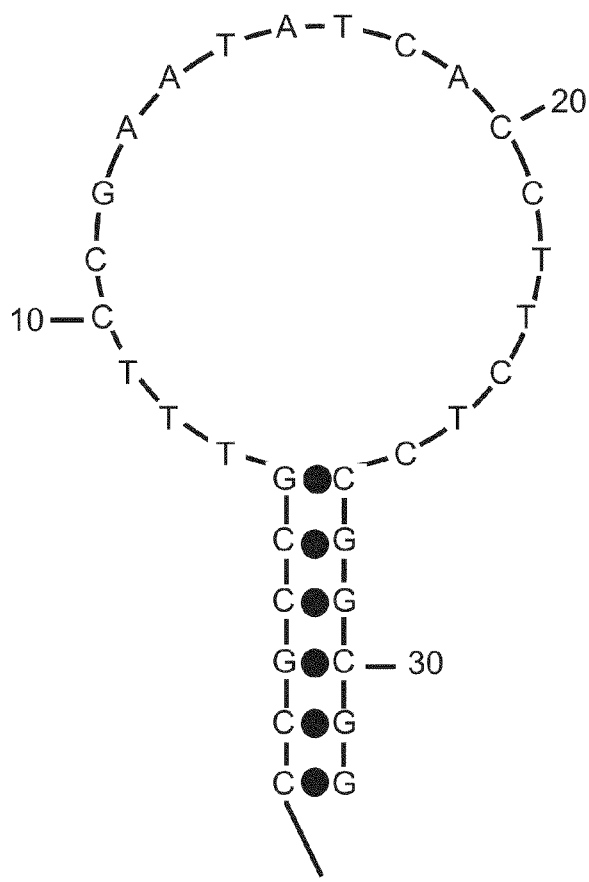
FIG. 11A shows the sequence of the congaa-hypFQ-1 molecular beacon (SEQ ID NO:4) and a complementary 14 nucleotide Abscript (SEQ ID NO:5). Restriction enzyme recognitions sites are underlined. Also shown are the extension product (SEQ ID NO:6) synthesized from the congaa-hypFQ-1 molecular beacon:Abscript hybrid and the cleavage sites generated by restriction enzyme Hpy188I.
FIG. 11B shows the stem and loop structure of the congaa-hypFQ-1 molecular beacon in 100 mM $Na^+$, 4.3 mM $Mg^+$ at 50° C.
Figure 11C:
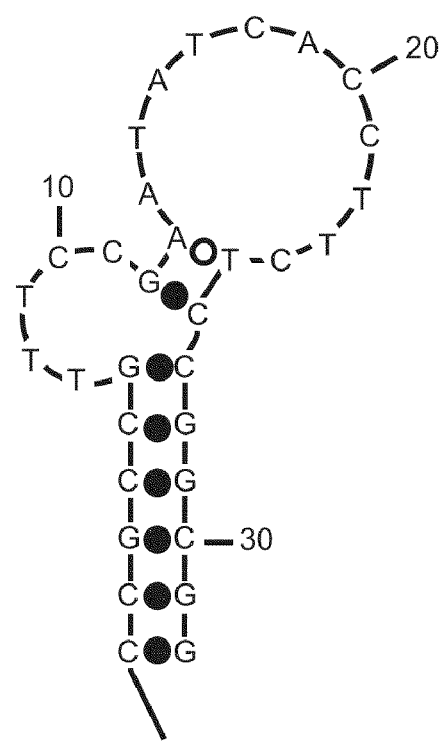
FIG. 11C and shows an alternate stem and loop structure of the congaa-hypFQ-1 molecular beacon ($T_m$ 53° C. in 50 mM $K^+$, 5 mM $Mg^{++}$).
Figure 11D:
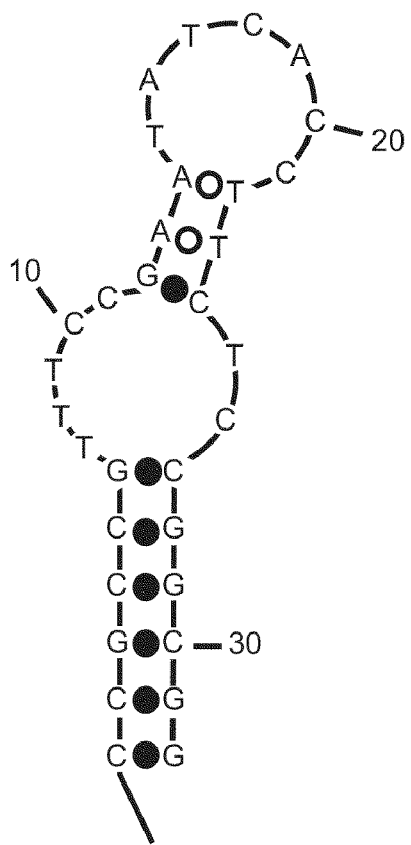
FIG. 11D shows a second alternate stem and loop structure of the congaa-hypFQ-1 molecular beacon ($T_m$ 48.5° C. in 50 mM $K^+$, 5 mM $Mg^{++}$).
Figure 11E:
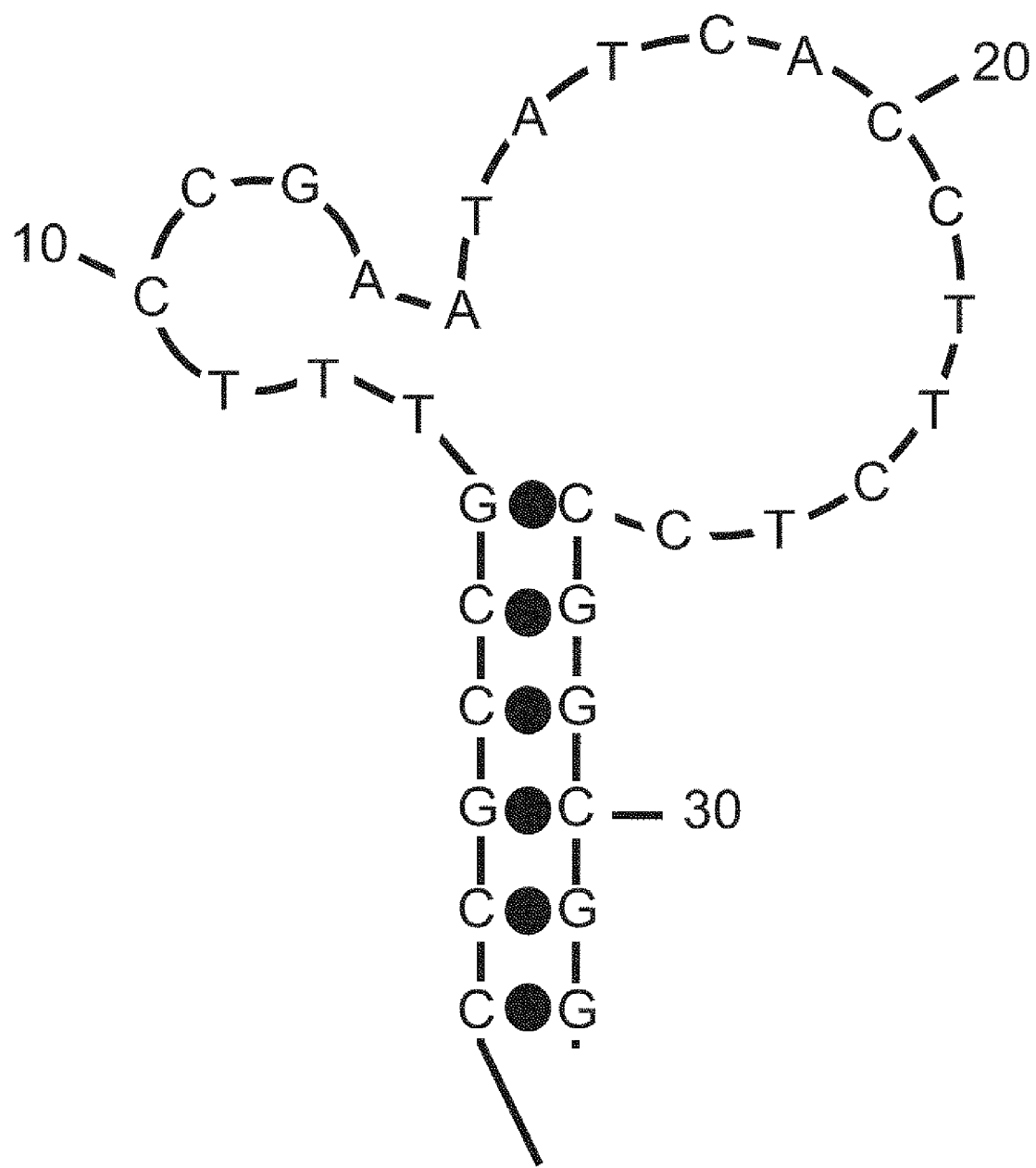
FIG. 11E shows a third alternate stem and loop structure of the congaa-hypFQ-1 molecular beacon ($T_m$ 49.5° C. in 50 mM $K^+$, 5 mM $Mg^{++}$).

Congaa-hpyFQ-1 Molecular Beacon. This beacon, the sequence of which is shown in FIG. 11A has a longer more stable stem than conGAA-1 (FIG. 11B). Alternative structures formed by this beacon are shown in FIGS. 11C-11E. The extension product of the complementary Abscript is 10 nt long and is cleaved with Hpy188I at 50° C.

Figures 12A, 12B:
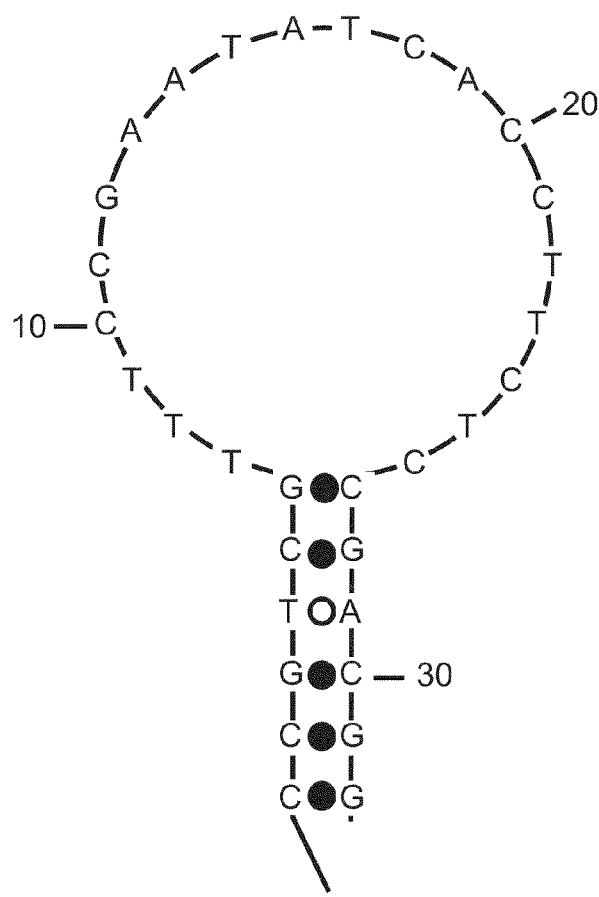
FIG. 12B shows the stem and loop structure of the congaa-hypFQ-2 molecular beacon ($T_m$ 62.1 in 50-100 mM $K^+$, 5 mM $Mg^+$).
Figure 12C:
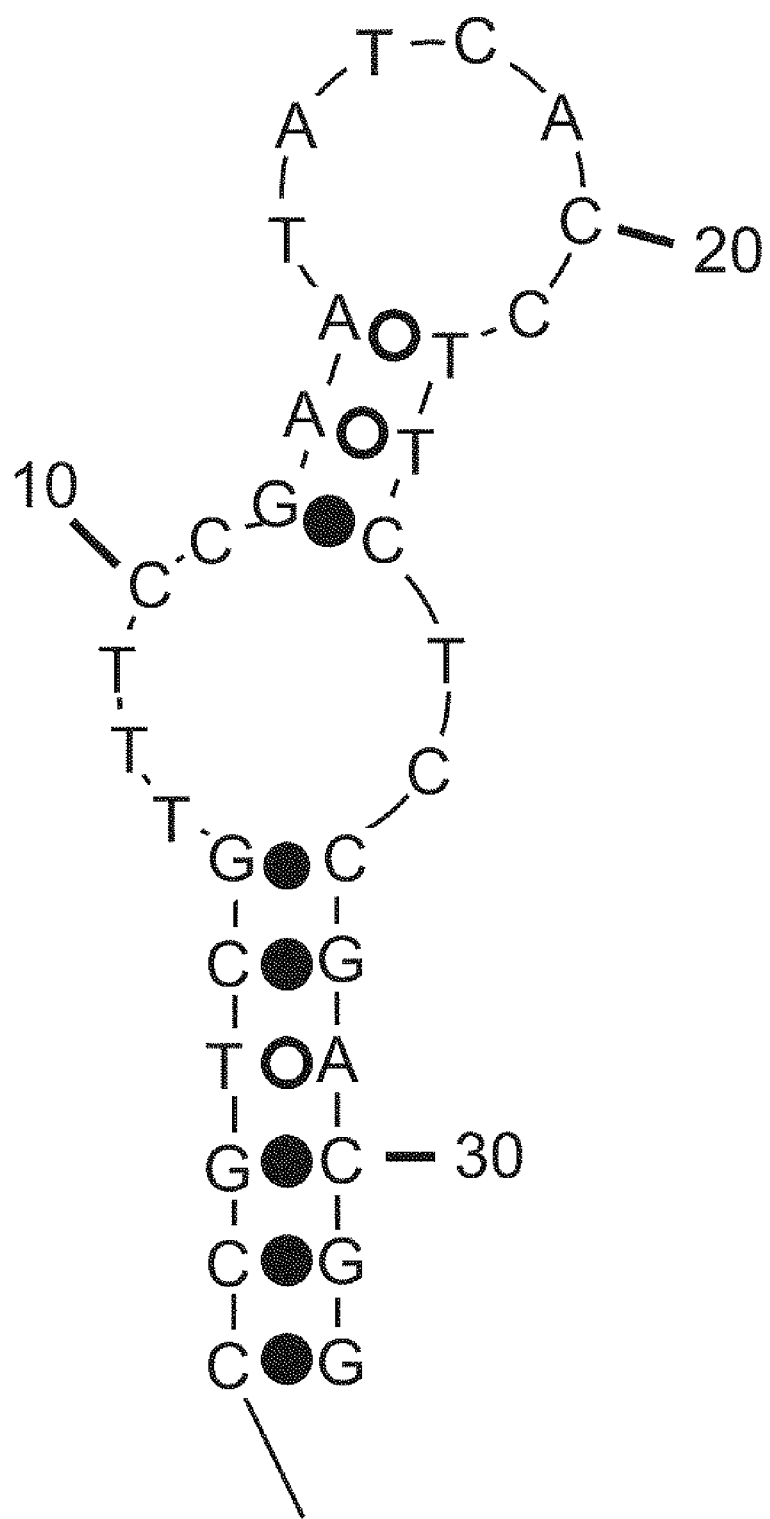
FIG. 12C shows an alternative second stem and loop structure of the congaa-hypFQ-2 molecular beacon ($T_m$ 45.4° C. in 100 mM $K^+$, 10 mM $Mg^+$).

Congaa-hpyFQ-2 Molecular Beacon. This beacon, the sequence of which is shown in FIG. 12A, is less stable than the congaa-hypFQ-1 (FIG. 12B). An alternative structure formed by this beacon is shown in FIG. 12C. As illustrated in the figure, less stable beacons, such as Congaa-hpyFQ-2, can be stabilized by the substitution of 2-amino-adenine for adenine.

Figures 13A, 13B:
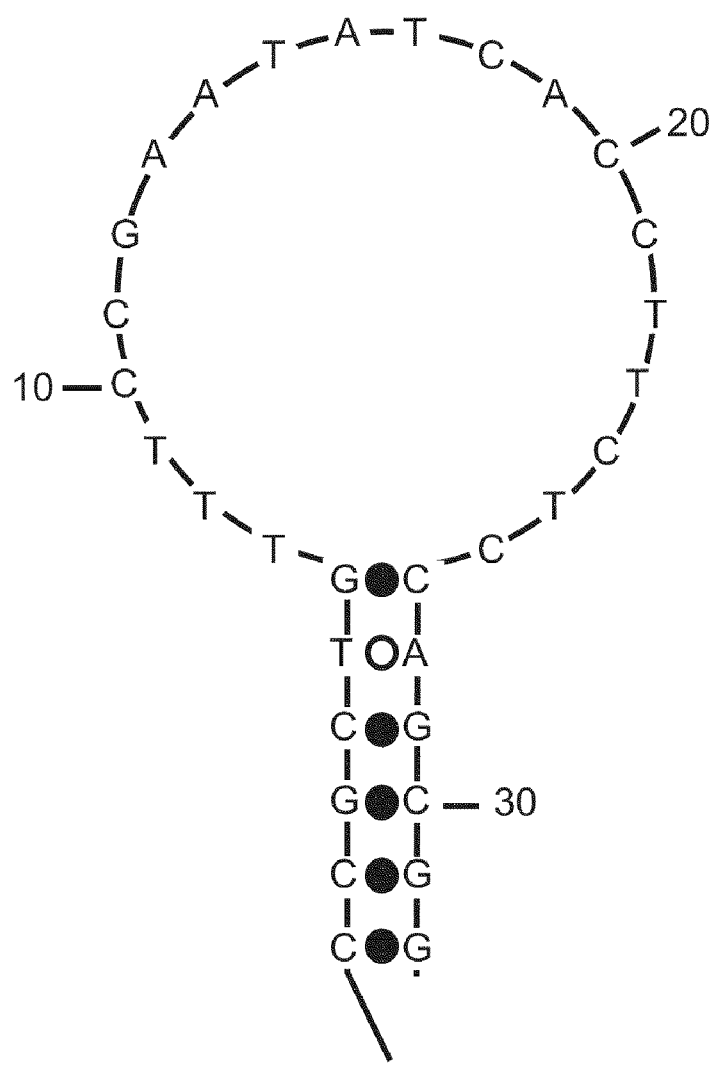
FIG. 13A shows the sequence of the congaa-hypFQ-3 molecular beacon (SEQ ID NO: 12).
FIG. 13B shows the stem and loop structure of the congaa-hypFQ-3 molecular beacon in 50 mM $K^+$, 5 mM $Mg^{++}$ ($T_m$ 63.5° C.), in 100 mM $K^+$, 5 mM $Mg^{++}$ ($T_m$ 64.3° C.) or 100 mM $K^+$, 10 mM $Mg^{++}$ ($T_m$ 65.9° C.).
Figure 13C:
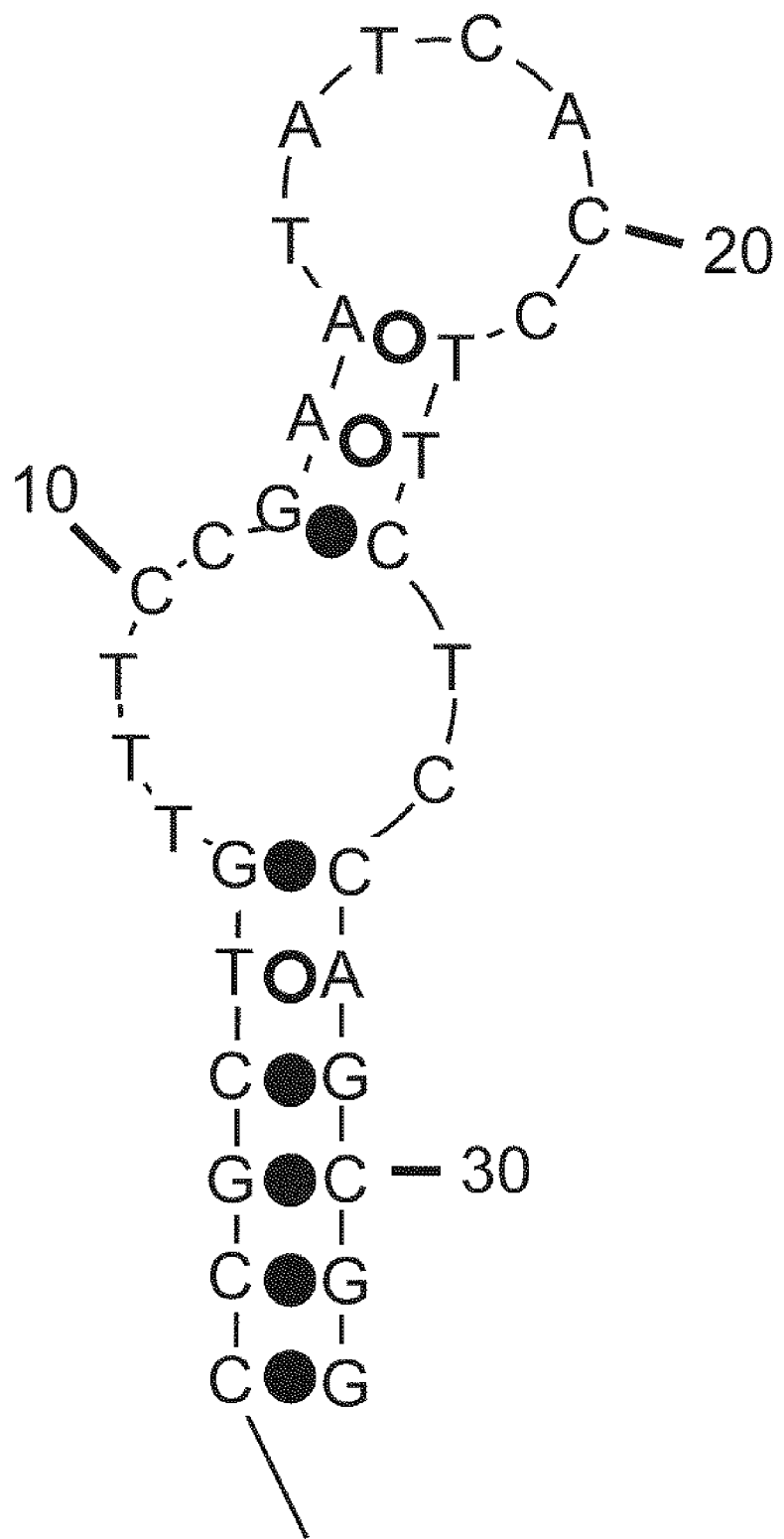
FIG. 13C shows an alternative stem and loop structure of the congaa-hypFQ-3 molecular beacon ($T_m$ 45.6° C. in 100 mM $K^+$, 10 mM $Mg^{++}$).

Congaa-hypFQ-3 Molecular Beacon. This beacon, the sequence of which is shown in FIG. 13A, also has a less stable stem than congaa-hpyFQ-1 (see FIG. 13B). An alternative structure formed by this beacon is shown in FIG. 13C.

Figures 14A, 14B:
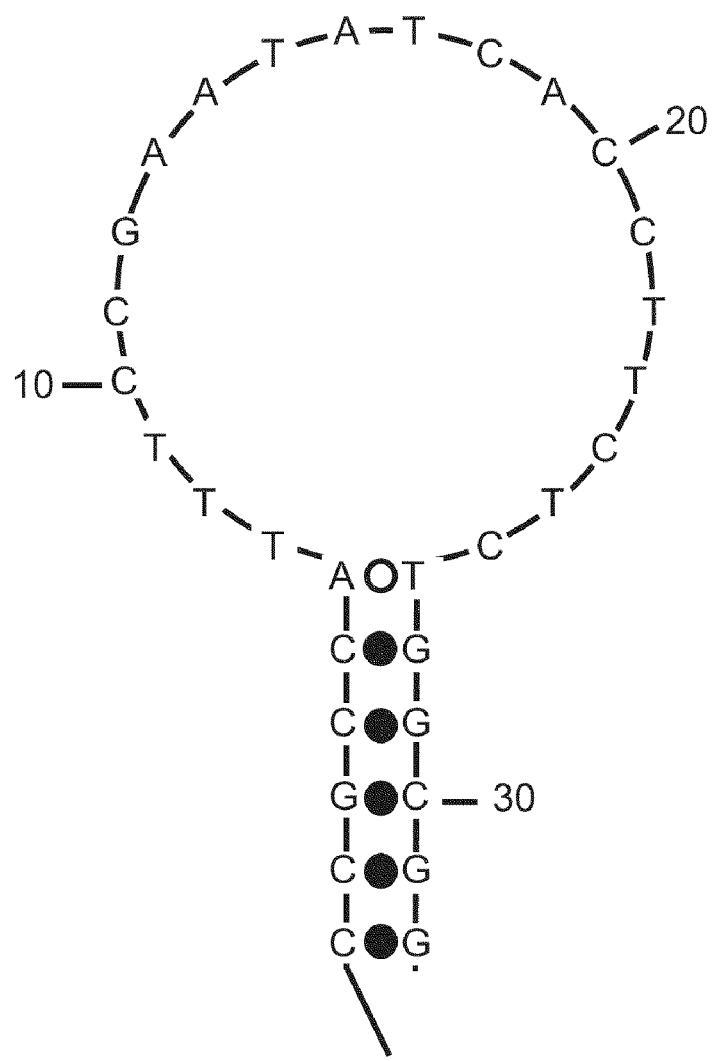
FIG. 14A shows the sequence of the alternated congaa-hypFQ-3 molecular beacon (SEQ ID NO:13).
FIG. 14B shows the stem and loop structure of derivative congaa-hypFQ-3 molecular beacon ($T_m$ 66.5° C.).
Figure 14C:
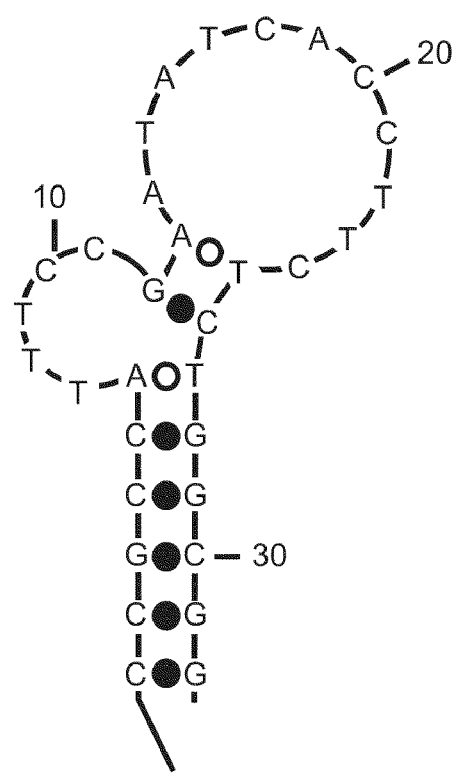
FIG. 14C shows an alternate stem and loop structure of the alternate congaa-hypFQ-3 molecular beacon ($T_m$ of 50.6° C.).
Figure 14D:
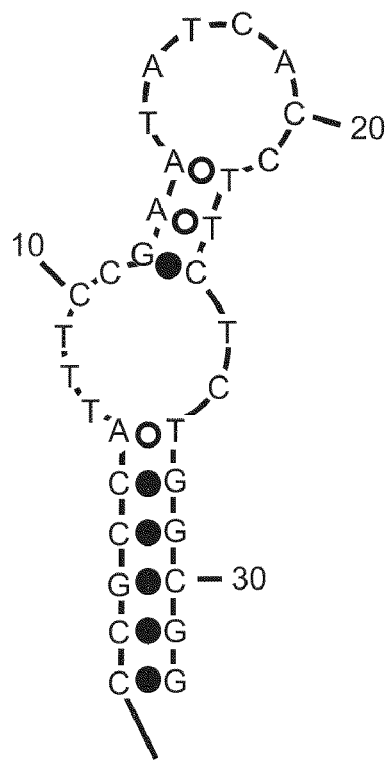
FIG. 14D shows a second alternative stem and loop structure of the derivative congaa-hypFQ-3 molecular beacon ($T_m$ of 45° C.).

Derivative Congaa-hypFQ-3 Molecular Beacon. This beacon, the sequence of which is shown in FIG. 14A, is derived from Congaa-hypFQ-3 by substituting an A:T bp at inner stem terminus to give alternative structures (FIGS. 14B-14D).

Figures 15A, 15B:
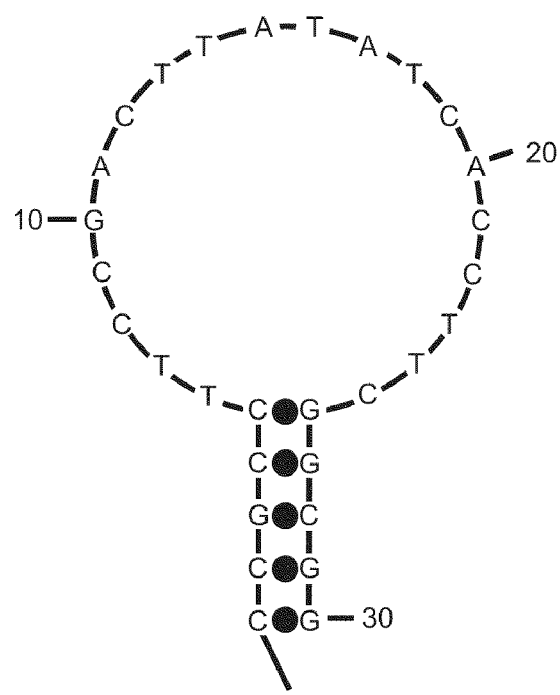
FIG. 15B shows the stem and loop structure of derivative HaeII molecular beacon with a $T_m$ of 63.1° C.

Derivative HaeII Molecular Beacon, is shown in FIG. 15A (sequence) and FIG. 15B (stem and loop structure).

What is claimed is:

1. A method for detecting a target comprising:
    a) performing an Abscription reaction synthesizing at least one Abscript, wherein synthesizing the at least one Abscript indicates the presence of a target;
    b) hybridizing the at least one Abscript synthesized in step a) to at least one molecular beacon, wherein the molecular beacon comprises a probe sequence complementary to the Abscript, thereby forming an Abscript:beacon hybrid;
    c) contacting the Abscript:beacon hybrid with a polymerase and nucleotides, thereby extending the Abscript in the Abscript:beacon hybrid and opening the molecular beacon; and
    d) detecting fluorescence from the opened molecular beacon, thereby detecting the target.

2. The method of claim 1, wherein the target is a protein or a nucleic acid.

3. The method of claim 1, wherein the at least one Abscript is an RNA sequence of 6-20 nucleotides in length.

4. The method of claim 3, wherein the at least one Abscript is 11 nucleotides in length.

5. The method of claim 1, wherein the steps a), b) and c) are performed in a single reaction.

6. A method for detecting a target comprising:
    a) performing an Abscription reaction synthesizing an Abscript, wherein synthesizing the Abscript indicates the presence of a target;
    b) hybridizing the Abscript synthesized in step a) to at least on first molecule of a molecular beacon, wherein the molecular beacon comprises a probe sequence complementary to the Abscript, thereby forming an Abscript:beacon hybrid;
    c) contacting the Abscript:beacon hybrid with a DNA polymerase and deoxyribonucleotides, thereby extending the Abscript in the Abscript: beacon hybrid, wherein extending the Abscript produces a double-strand DNA sequence recognized by a restriction enzyme;
    d) digesting the double-strand DNA sequence with the restriction enzyme, thereby producing a fluorophore fragment and an extended Abscript fragment; and
    e) detecting fluorescence from the fluorophore fragment, thereby detecting the target.

7. The method of claim 6, wherein the restriction enzyme is selected from HaeII, HhaI, HinPI and Hpy188I.

8. The method of claim 3, further comprising:
    f) hybridizing the extended Abscript fragment of step d) with a second molecule of the molecular beacon, thereby forming an extended Abscript fragment:beacon hybrid;
    g) contacting the extended Abscript fragment:beacon hybrid with a DNA polymerase and deoxyribonucleotides, thereby re-extending the extended Abscript fragment in the extended Abscript fragment:probe hybrid, wherein extending the extended Abscript fragment produces a double-strand DNA sequence recognized by the restriction enzyme;
    h) digesting the double-strand DNA sequence with the restriction enzyme, thereby producing a fluorophore fragment and an extended Abscript fragment;
    i) repeating steps f) through h); and
    j) detecting fluorescence of the fluorophore fragment, thereby detecting the target.

9. The method of claim 8, wherein the steps a) through i) are performed in a single reaction.

10. The method of claim 8, wherein steps f) through h) are repeated at least 10 times.

11. A method for detecting at least two targets comprising:
    a) performing a first Abscription reaction synthesizing a first Abscript, wherein synthesizing the first Abscript indicates the presence of a first target;
    b) performing a second Abscription reaction synthesizing a second Abscript having a different nucleotide sequence than the first Abscript, wherein synthesizing the second Abscript indicates the presence of a second target;
    c) hybridizing the first Abscript synthesized in step a) with a first molecular beacon comprising a first fluorophore, wherein the first molecular beacon comprises a probe sequence complementary to the first Abscript, thereby forming a first Abscript:beacon hybrid;
    d) -hybridizing the second Abscript synthesized in step b) with a second molecular beacon comprising a second fluorphore that fluoresces at a different wavelength from the first fluorophore, wherein the second molecular beacon comprises a probe sequence complementary to the second Abscript, thereby forming a second Abscript:beacon hybrid;

e) contacting the first and second Abscript:beacon hybrids with a polymerase and nucleotides, thereby extending the first and second Abscripts in the Abscript:beacon hybrids and opening the first and second molecular beacons; and f) detecting fluorescence of the first and second opened molecular beacons, thereby detecting the two targets.

12. The method of claim 11, wherein steps a)-f) are performed in a single reaction.

13. A method of detecting a target in plurality of samples, comprising:

a) performing an Abscription reaction for each of a plurality of samples, synthesizing at least one Abscript, wherein synthesizing the at least one Abscript indicates the presence of a target;

b) hybridizing the at least one Abscript synthesized in step a) with at least one molecular beacon, wherein the molecular beacon comprises a probe sequence complementary to the Abscript to form an Abscript:beacon hybrid;

c) contacting the Abscript:beacon hybrid with a polymerase and nucleotides, thereby extending the Abscripts in the Abscript:beacon hybrids thereby opening the molecular beacon; and d) detecting fluorescence of the opened molecular beacon, thereby detecting the target.

14. The method of claim 13, wherein each sample is from a different source and the same target is detected in each sample.

15. The method of claim 13, wherein each sample is the same, and the target detected in each sample is different.

16. The method of claim 1, wherein the polymerase is a DNA polymerase.

17. The method of claim 11, wherein the polymerase is a DNA polymerase.

18. The method of claim 13, wherein the polymerase is a DNA polymerase.

* * * * *

SEQUENCE LISTING

```
<160> NUMBER OF SEQ ID NOS: 14

<210> SEQ ID NO 1
<211> LENGTH: 31
<212> TYPE: DNA
<213> ORGANISM: Artificial Sequence
<220> FEATURE:
<223> OTHER INFORMATION: synthetic oligonucleotide molecular beacon

<400> SEQUENCE: 1
ccgcctagcg ctcttatatc accttcggcg g                                      31

<210> SEQ ID NO 2
<211> LENGTH: 11
<212> TYPE: RNA
<213> ORGANISM: Artificial Sequence
<220> FEATURE:
<223> OTHER INFORMATION: synthetic oligonucleotide abscript

<400> SEQUENCE: 2
gaaggugaua u                                                            11

<210> SEQ ID NO 3
<211> LENGTH: 26
<212> TYPE: DNA
<213> ORGANISM: Artificial Sequence
<220> FEATURE:
<223> OTHER INFORMATION: synthetic oligonucleotide extended from conGAA
      abscript:beacon hybrid
```

```
<400> SEQUENCE: 3
gaaggugaua uaagagcgct aggcgg                                            26

<210> SEQ ID NO 4
<211> LENGTH: 32
<212> TYPE: DNA
<213> ORGANISM: Artificial Sequence
<220> FEATURE:
<223> OTHER INFORMATION: synthetic oligonucleotide molecular beacon

<400> SEQUENCE: 4
ccgccgtttc cgaatatcac cttctccggc gg                                     32

<210> SEQ ID NO 5
<211> LENGTH: 11
<212> TYPE: RNA
<213> ORGANISM: Artificial Sequence
<220> FEATURE:
<223> OTHER INFORMATION: synthetic oligonucleotide abscript

<400> SEQUENCE: 5
gaaggugaua u                                                            11

<210> SEQ ID NO 6
<211> LENGTH: 25
<212> TYPE: DNA
<213> ORGANISM: Artificial Sequence
<220> FEATURE:
<223> OTHER INFORMATION: synthetic oligonucleotide extended from
      conGAA-hpyFQ-1 abscript:beacon hybrid

<400> SEQUENCE: 6
gaaggugaua utcggaaaac ggcgg                                             25

<210> SEQ ID NO 7
<211> LENGTH: 32
<212> TYPE: DNA
<213> ORGANISM: Artificial Sequence
<220> FEATURE:
<223> OTHER INFORMATION: synthetic oligonucleotide molecular beacon

<400> SEQUENCE: 7
ccgtcgtttc cgaatatcac cttctccgac gg                                     32

<210> SEQ ID NO 8
<211> LENGTH: 11
<212> TYPE: RNA
<213> ORGANISM: Artificial Sequence
<220> FEATURE:
<223> OTHER INFORMATION: synthetic oligonucleotide abscript

<400> SEQUENCE: 8
gaaggugaua u                                                            11

<210> SEQ ID NO 9
<211> LENGTH: 32
<212> TYPE: DNA
<213> ORGANISM: Artificial Sequence
<220> FEATURE:
<223> OTHER INFORMATION: synthetic oligonucleotide molecular beacon
<220> FEATURE:
<221> NAME/KEY: 2-amino-adenine
<222> LOCATION: (16)..(16)
<220> FEATURE:
<221> NAME/KEY: misc_feature
<222> LOCATION: (16)..(16)
<223> OTHER INFORMATION: n is a, c, g, or t
```

```
<220> FEATURE:
<221> NAME/KEY: 2-amino-adenine
<222> LOCATION: (19)..(19)
<220> FEATURE:
<221> NAME/KEY: misc_feature
<222> LOCATION: (19)..(19)
<223> OTHER INFORMATION: n is a, c, g, or t

<400> SEQUENCE: 9
ccgtcgtttc cgaatntcnc cttctccgac gg                                     32

<210> SEQ ID NO 10
<211> LENGTH: 32
<212> TYPE: DNA
<213> ORGANISM: Artificial Sequence
<220> FEATURE:
<223> OTHER INFORMATION: synthetic oligonucleotide molecular beacon
<220> FEATURE:
<221> NAME/KEY: 2-amino-adenine
<222> LOCATION: (14)..(14)
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: 2-amino-adenine
<222> LOCATION: (16)..(16)
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: 2-amino-adenine
<222> LOCATION: (19)..(19)
<220> FEATURE:
<221> NAME/KEY: misc_feature
<222> LOCATION: (19)..(19)
<223> OTHER INFORMATION: n is a, c, g, or t

<400> SEQUENCE: 10
ccgtcgtttc cgantntcnc cttctccgac gg                                     32

<210> SEQ ID NO 11
<211> LENGTH: 11
<212> TYPE: RNA
<213> ORGANISM: Artificial Sequence
<220> FEATURE:
<223> OTHER INFORMATION: synthetic oligonucleotide abscript
<220> FEATURE:
<221> NAME/KEY: 2-amino-adenine
<222> LOCATION: (2)..(3)
<220> FEATURE:
<221> NAME/KEY: misc_feature
<222> LOCATION: (2)..(3)
<223> OTHER INFORMATION: n is a, c, g, or u
<220> FEATURE:
<221> NAME/KEY: 2-amino-adenine
<222> LOCATION: (10)..(10)
<220> FEATURE:
<221> NAME/KEY: misc_feature
<222> LOCATION: (10)..(10)
<223> OTHER INFORMATION: n is a, c, g, or u

<400> SEQUENCE: 11
gnnggugcun u                                                            11

<210> SEQ ID NO 12
<211> LENGTH: 32
<212> TYPE: DNA
<213> ORGANISM: Artificial Sequence
<220> FEATURE:
<223> OTHER INFORMATION: synthetic oligonucleotide molecular beacon

<400> SEQUENCE: 12
```

```
ccgctgtttc cgaatatcac cttctccagc gg                                    32

<210> SEQ ID NO 13
<211> LENGTH: 32
<212> TYPE: DNA
<213> ORGANISM: Artificial Sequence
<220> FEATURE:
<223> OTHER INFORMATION: synthetic polynucleotide molecular beacon

<400> SEQUENCE: 13
ccgccatttc cgaatatcac cttctctggc gg                                    32

<210> SEQ ID NO 14
<211> LENGTH: 30
<212> TYPE: DNA
<213> ORGANISM: Artificial Sequence
<220> FEATURE:
<223> OTHER INFORMATION: synthetic polynucleotide molecular beacon

<400> SEQUENCE: 14
ccgccttccg acttatatca ccttcggcgg                                       30
```